(12) United States Patent
Phan et al.

(10) Patent No.: US 6,872,711 B2
(45) Date of Patent: Mar. 29, 2005

(54) β-SUBSTITUTED β-AMINOETHYL PHOSPHONATE DERIVATIVES

(75) Inventors: Hieu Trung Phan, Tannay (CH); Lan Mong Nguyen, Nyon (CH); Vinh Van Diep, Vetraz-Monthoux (FR); Raymond Azoulay, Geneva (CH); Eric Joseph Niesor, Nyon (CH); Craig Leigh Bentzen, Bogis-Dossey (CH); Robert John Ife, Stevenage (GB)

(73) Assignee: Ilex Oncology Research S.A., Geneva (CH)

( * ) Notice: Subject to any disclaimer, the term of this patent is extended or adjusted under 35 U.S.C. 154(b) by 31 days.

(21) Appl. No.: 10/012,785

(22) Filed: Oct. 22, 2001

(65) Prior Publication Data
US 2002/0111488 A1 Aug. 15, 2002

(30) Foreign Application Priority Data
Oct. 23, 2000 (GB) .......................................... 00258491

(51) Int. Cl.⁷ .................. A61K 31/675; A61K 31/505; A61K 31/40; C07D 211/70
(52) U.S. Cl. ........................ 514/89; 546/22; 546/24; 514/89; 514/256; 514/406; 544/243; 548/375.1
(58) Field of Search ............... 546/24, 22; 514/89, 514/256, 406; 548/375.1; 544/243

(56) References Cited

U.S. PATENT DOCUMENTS

| | | | |
|---|---|---|---|
| 5,424,303 A | 6/1995 | Phan et al. | 514/89 |
| 5,441,946 A | 8/1995 | Pauls et al. | 514/114 |
| 6,060,464 A | * 5/2000 | Nguyen et al. | 514/89 |
| 6,117,873 A | 9/2000 | Acklin et al. | 514/249 |
| 6,303,784 B1 | * 10/2001 | Nguyen et al. | 546/24 |

FOREIGN PATENT DOCUMENTS

| | | | |
|---|---|---|---|
| CA | 2158517 | 9/1995 | C07F/9/38 |
| JP | 07059765 | 2/1995 | C07F/9/553 |
| WO | PCT/GB97/03479 | 12/1997 | C07F/9/58 |
| WO | PCT/EP97/07192 | 12/1997 | C07F/9/58 |

OTHER PUBLICATIONS

Surpak et al.; "Investigation on antibacterial activity of some new aminophosphinic and aminophosphonic complexons," *Pharmazie*, 1981:36:782–783.

Co–Pending U.S. application No. 09/963,900, by H. T. Phan et al., field Sep. 26, 2001.

Karimov et al., Necleophilic Addition of Amines to Dialkyl 1–Phenylethenyl–Phosphonate, J. Gen Chem. USSR 59:904–905, 1989.

Ing, "The Pharmacology of Homolous Series," pp. 306–309, In: Progress in Drug Research, Ed. Jucker, Birkhaeuser verlag, vol. 7. 1964.

* cited by examiner

*Primary Examiner*—Ceila Chang
*Assistant Examiner*—Janet Coppins
(74) *Attorney, Agent, or Firm*—Fulbright & Jaworski L.L.P.

(57) ABSTRACT

The present invention relates to novel β-substituted-β-aminoethylphosphonate derivatives and their uses for lowering plasma levels of apo (a), Lp(a), apo B, apo B associated lipoproteins (low density lipoproteins and very low density lipoproteins) and for lowering plasma levels of total cholesterol.

16 Claims, No Drawings

β-SUBSTITUTED β-AMINOETHYL PHOSPHONATE DERIVATIVES

This application claims priority to United Kingdom Application No. GB00258491.1 filed Oct. 23, 2000.

FIELD OF THE INVENTION

This invention relates to substituted aminoethylphosphonate compositions and therapeutic uses thereof. More specifically, the present invention relates to novel β-substituted-β-aminoethylphosphonate derivatives, processes for their preparations, pharmaceutical compositions containing them and their use in therapy, for lowering plasma levels of apo (a) and apo (a) associated lipoprotein (lipoprotein(a) or "Lp(a)"), for lowering plasma levels of apo B and apo B associated lipoproteins (low density lipoproteins and very low density lipoproteins), and for lowering plasma levels of total cholesterol.

BACKGROUND OF THE INVENTION

Lp(a) is a LDL-like lipoprotein wherein the major lipoprotein, apo B-100, is covalently linked to an unusual glycoprotein, apoprotein(a). The covalent association between apo(a) and apo B to form Lp(a) is a secondary event which is independent of the plasma concentration of apo B. Due to its structural similarity to plasminogen, apo(a) interferes with the normal physiological thrombosis-hemostasis process by preventing thrombolysis, that is clot dissolution (see e.g., Biemond B J, Circulation 1997, 96(5) 1612–1615). The structural feature of Lp(a), where the LDL lipoprotein is linked to apo(a), is thought to be responsible for its atherogenic and thrombogenic activities.

Elevated levels of Lp(a) have been associated with the development of atherosclerosis, coronary heart disease, myocardial infarction, cerebral infarction, restenosis following balloon angioplasty and stroke. A recent epidemiologic study has provided the clinical proof of a positive correlation between plasma Lp(a) concentrations and the incidence of heart disease (A. G. Bostom, et al., Journal of American Medical Association 1996, 276, p. 544–548).

Patients that have Lp(a) levels in excess of 20–30 mg/dl run a significantly increased risk of heart attacks and stroke. An effective therapy for lowering Lp(a) does not exist at present because cholesterol-lowering agents such as the HMGCoA reductase inhibitors do not lower Lp(a) plasma concentrations. The only compound that lowers Lp(a) is niacin, but the high doses necessary for activity are accompanied with unacceptable side effects. There is, therefore, an unmet therapeutic need for agents that effectively reduce elevated levels of Lp(a).

International applications WO 97/20307, WO 98/28310, WO 98/28311 and WO 98/28312 (Symphar, SmithKline Beecham) describe a series of α-amino phosphonates which have Lp(a) lowering activity. There however remains the need to identify further compounds having Lp(a) lowering activity.

SUMMARY OF THE INVENTION

The present invention provides, in a first aspect, a compound of formula (I):

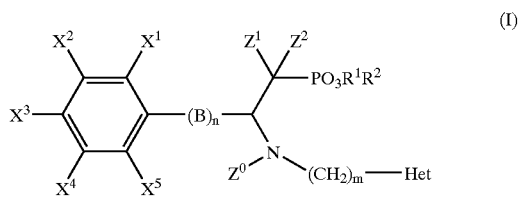

in which:
$X^1$, $X^2$, $X^3$, $X^4$ and $X^5$ are independently hydrogen, hydroxy, hydroxymethyl, $C_1$–$C_2$ alkoxymethyl, a straight or branched $C_1$–$C_8$ alkyl group, a straight or branched $C_1$–$C_8$ alkoxy group; or
$X^2$ may be combined with $X^3$ or $X^4$ may be combined with $X^5$ to form a 5- to 6-membered alkylidenedioxy ring optionally substituted with $C_1$ to $C_4$ alkyl groups; or
$X^4$ may be combined with $X^5$ to form a 5- to 6-membered alkylidene ring optionally substituted with $C_1$ to $C_4$ alkyl groups;
$R^1$ and $R^2$ are independently H, a straight or branched alkyl group having from 1 to 6 carbon atoms;
B is $CH_2$, $CH_2$—$CH_2$ or CH=CH;
n is zero or 1;
$Z^0$ is H, a straight or branched alkyl group having from 1 to 4 carbon atoms, an acyl group
$R^3$—CO where $R^3$ is an alkyl group from 1 to 4 carbon atoms, a perfluoroalkyl group from 1 to 4 carbon atoms;
$Z^1$, $Z^2$ are independently H, Cl, Br, F, a straight or branched alkyl group from 1 to 4 carbon atoms;
m is zero to 4;
Het is an optionally substituted heteroaryl group comprising at least one nitrogen atom; or
a pharmaceutically acceptable salt thereof.

Compounds of the present invention include:

diethyl β-(3,5-dimethoxy-4-hydroxyphenyl)-β-[N-(3-pyridyl)-amino]-ethylphosphonate;
diisopropyl β-(3,5-dimethoxy-4-hydroxyphenyl)-β-[N-(3-pyridyl)-amino]-ethylphosphonate;
diethyl β-(3,5-dimethoxy-4-hydroxyphenyl)-β-[N-5-(2-methylpyridyl)-amino]-ethylphosphonate;
diisopropyl β-(3,5-dimethoxy-4-hydroxyphenyl)-β-[N-5-(2-methylpyridyl)-amino]-ethylphosphonate;
diethyl β-(3,5-dimethoxy-4-hydroxyphenyl)-β-[N-(3-(2,6-dimethyl)pyridyl))-amino]-ethylphosphonate;
diisopropyl β-(3,5-dimethoxy-4-hydroxyphenyl)-β-[N-(3-(2,6-dimethyl)pyridyl))-amino]-ethylphosphonate;
diethyl β-(3,5-dimethoxy-4-hydroxyphenyl)-β-[N-5-(2-methoxypyridyl)-amino]-ethylphosphonate;
diisopropyl β-(3,5-dimethoxy-4-hydroxyphenyl)-β-[N-5-(2-methoxypyridyl)-amino]-ethylphosphonate;
diethyl β-(4-hydroxy-3-methoxy-5-methylphenyl)-β-[N-(3-pyridyl)-amino]-ethylphosphonate;
diisopropyl β-(4-hydroxy-3-methoxy-5-methylphenyl)-β-[N-(3-pyridyl)-amino]-ethylphosphonate;
diethyl β-(4-hydroxy-3-methoxy-5-methylphenyl)-β-[N-5-(2-methylpyridyl)-amino]-ethylphosphonate;
diisopropyl β-(4-hydroxy-3-methoxy-5-methylphenyl)-β-[N-5-(2-methylpyridyl)-amino]-ethylphosphonate;
dimethyl β-(4-hydroxy-3-methoxy-5-methylphenyl)-β-[N-(3-(2,6-dimethyl)pyridyl)-amino]-ethylphosphonate;
diethyl β-(4-hydroxy-3-methoxy-5-methylphenyl)-β-[N-(3-(2,6-dimethyl)pyridyl)-amino]-ethylphosphonate;
diisopropyl β-(4-hydroxy-3-methoxy-5-methylphenyl)-β-[N-(3-(2,6-dimethyl)pyridyl)-amino]-ethylphosphonate;
diethyl β-(3,5-dimethyl-4-hydroxyphenyl)-β-[N-(3-pyridyl)-amino]-ethylphosphonate;

diisopropyl β-(3,5-dimethyl-4-hydroxyphenyl)-β-[N-(3-pyridyl)-amino]-ethylphosphonate;
diethyl β-(3,4,5-trimethoxyphenyl)-β-[N-(3-pyridyl)-amino]-ethylphosphonate;
diisopropyl β-(3,4,5-trimethoxyphenyl)-β-[N-(3-pyridyl)-amino]-ethylphosphonate;
diethyl β-(3-ethoxy-4-hydroxy-5-methylphenyl)-β-[N-(3-pyridyl)-amino]-ethylphosphonate;
diisopropyl β-(3-ethoxy-4-hydroxy-5-methylphenyl)-β-[N-(3-pyridyl)-amino]-ethylphosphonate;
diethyl β-(3-ethoxy-4-hydroxy-5-methylphenyl)-β-[N-(3-(2,6-dimethyl)pyridyl)]-ethylphosphonate;
diisopropyl β-(3-ethoxy-4-hydroxy-5-methylphenyl)-β-[N-(3-(2,6-dimethyl)pyridyl)]-ethylphosphonate;
diethyl β-(4,5-dimethoxy-3-hydroxyphenyl)-β-[N-(3-(2,6-dimethylpyridyl))-amino]-ethylphosphonate;
diisopropyl β-(4,5-dimethoxy-3-hydroxyphenyl)-β-[N-(3-(2,6-dimethylpyridyl))-amino]-ethylphosphonate;
diethyl β-(3-hydroxy-4-methoxy-5-methylphenyl)-β-[N-(3-(2,6-dimethylpyridyl))-amino]-ethylphosphonate;
diisopropyl β-(3-hydroxy-4-methoxy-5-methylphenyl)-β-[N-(3-(2,6-dimethylpyridyl))-amino]-ethylphosphonate;
diethyl β-(4-hydroxy-3-methoxy-5-methylphenyl)-β-[N-(3-(2,6-dimethyl)pyridyl))-amino]-α-methyl-ethylphosphonate;
diethyl β-(4-hydroxy-3-methoxy-5-methylphenyl)-β-[N-(3-(2,6-dimethyl)pyridyl))-amino]-α,α-difluoro-ethylphosphonate;
diethyl β-(3,5-di-tert-butyl-4-methoxyphenyl)-β-[N-(3-pyridyl)-amino]-ethylphosphonate;
diethyl β-(2,4-dimethyl-3-hydroxyphenyl)-β-[N-(3-pyridyl)-amino]-ethylphosphonate;
diethyl β-(2,4-dimethyl-3-hydroxyphenyl)-β-[N-(5-(2-methylpyridyl))-amino]-ethylphosphonate;
diethyl β-(2,4-dimethyl-3-hydroxyphenyl)-β-[N-(3-(2,6-dimethylpyridyl))-amino]-ethylphosphonate;
diethyl β-(3-hydroxy-5-methoxy-4-methylphenyl)-β-[N-(3-pyridyl)-amino]-ethylphosphonate;
diethyl β-(3-hydroxy-5-methoxy-4-methylphenyl)-β-[N-(5-(2-methylpyridyl))-amino]-ethylphosphonate;
diethyl β-(3-hydroxy-5-methoxy-4-methylphenyl)-β-[N-(3-(2,6-dimethylpyridyl))-amino]-ethylphosphonate;
diethyl β-(3,5-dimethoxy-4-hydroxymethylphenyl)-β-[N-(3-pyridyl)-amino]-ethylphosphonate;
diethyl β-(3,5-dimethoxy-4-hydroxymethylphenyl)-β-[N-(5-(2-methylpyridyl))-amino]-ethylphosphonate; and
diethyl β-(3,5-dimethoxy-4-hydroxymethylphenyl)-β-[N-(3-(2,6-dimethylpyridyl))-amino]-ethylphosphonate.

One aspect of the present invention provides for a pharmaceutical composition comprising a compound of formula (I) and a pharmaceutically acceptable excipient.

The present invention also provides for therapeutic uses of the compounds of formula (I). In one aspect, the invention provides for a method of decreasing plasma levels of apo (a) and lipoprotein(a), in reducing plasma levels of apo B and LDL cholesterol and in decreasing plasma total cholesterol. The present invention also provides further methods including: a method of treatment and/or prevention of thrombosis by increasing thrombolysis through decreasing plasma levels of apo (a) and lipoprotein(a); a method of treatment of restenosis following angioplasty by decreasing plasma levels of apo (a) and lipoprotein(a); a method of prevention and/or treatment of atherosclerosis by decreasing plasma levels of apo (a) and lipoprotein(a) or by decreasing plasma levels of apoprotein B and LDL cholesterol; a method of prevention and/or treatment of hypercholesterolemia; a method of prevention and/or treatment of atherosclerosis by lowering cholesterol in patients that are resistant to treatment with statins; and a method of prevention and/or treatment of atherosclerosis in association with a compound such as a statin which decreases cholesterol synthesis.

DETAILED DESCRIPTION OF THE INVENTION

The present invention relates to the compounds of formula (I) and their uses for lowering plasma levels of apo (a), Lp(a), apo B, apo B associated lipoproteins (low density lipoproteins and very low density lipoproteins) and for lowering plasma levels of total cholesterol.

In relation to compounds of formula (I), in preferred embodiments $X^1$ is hydrogen or methyl; $X^2$ is methoxy, ethoxy, methyl or hydroxy; $X^3$ is hydrogen, hydroxy, methoxy, hydroxymethyl, methoxymethyl, methyl or ethyl; $X^4$ is hydrogen, methoxy or methyl and $X^5$ is hydrogen. Preferably, n=0, so that $(B)_n$ is replaced with a direct bond, or n is 1 and B is $CH_2$. In other preferred embodiments, $R^1$ and $R^2$ are independently a $C_1–C_3$ alkyl group, and more preferably a $C_2$ or $C_3$ group, in particular, an ethyl or isopropyl group. In further preferred embodiments, m is zero, $Z^0$ is hydrogen and $Z^1$ and $Z^2$ are each hydrogen.

When used herein the term "heteroaryl" refers to, unless otherwise defined, a single or a fused ring containing up to four heteroatoms in each ring, each of which is selected from oxygen, nitrogen and sulphur, which rings, may be unsubstituted or substituted by, for example, up to four substituents. Each ring suitably has from 4 to 7, preferably 5 or 6, ring atoms. A fused ring system may include carbocyclic rings and need include only one heteroaryl ring.

Representative examples of Het include pyridyl, pyrimidyl, pyrazyl and triazinyl which may be unsubstituted or substituted by up to four substituents (for pyridyl), three substituents (pyrimidyl, pyrazyl), or two substituents (triazinyl) which may be the same or different and selected from straight or branched $C_1–C_4$ alkyl or alkoxy, hydroxy, hydroxymethyl, halogen (F, Cl, Br, I), or an amino group optionally substituted with $C_1–C_4$ alkyl. Preferably, Het is pyridyl, pyrimidyl, pyrazyl which is unsubstituted or substituted by methyl, methoxy, dimethoxy or dimethyl. A preferred example of Het is 3-pyridyl or 3-(2,6-dimethylpyridyl).

Pharmaceutically acceptable salts for use in the present invention include those described by Berge, Bighley, and Monkhouse, *J. Pharm. Sci.*, 1977, 66, 1–19. Such salts may be formed from inorganic and organic acids. Representative examples thereof include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Compounds of formula (I) are racemates as they have at least one chiral center which is the carbon atom in position beta to the phosphonate group. The compounds of formula (I) therefore exist in the two enantiomeric forms. The racemic mixtures (approximately 50% of each enantiomer), other mixtures of the enantiomers and the pure enantiomers are comprised in the scope of this application. Likewise, compounds of formula (I) where $Z^1$ and $Z^2$ are not identical may exist as a mixture of diastereoisomers. The mixtures and the individual isomers are also encompassed by the present invention. Unless otherwise indicated, the physical constants and biological data given for compounds of formula (I) refer to racemates and mixtures of diastereoisomers.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (1) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

The present invention further relates to the unexpected discovery that compounds of formula (I) are effective for decreasing apo(a) production in vitro and Lp(a) production in vivo in Cynomolgus monkeys. This species has been selected as the animal model as its Lp(a) is similar in immunologic properties to human Lp(a) and occurs in almost identical frequency distribution of plasma concentrations, see for instance N. Azrolan et al; J. Biol. Chem., 266, 13866–13872 (1991). In the in vitro assay, compounds of formula (I) have been shown to reduce the secretion of apo (a) which is secreted in free form from the primary cultures of the Cynomolgus monkey hepatocytes. These results are confirmed by the in vivo studies performed on the same animal species showing the potent decrease of Lp(a) by compounds of formula (I). Therefore the compounds of this invention are useful for decreasing apo (a) and Lp(a) in man and thus provide a therapeutic benefit.

Accordingly in a further aspect, this invention provides a compound of formula (I) or a pharmaceutically acceptable salt thereof for use in therapy, in particular as a Lp(a) lowering agent. Elevated plasma and tissue levels of Lp(a) are associated with accelerated atherosclerosis, abnormal proliferation of smooth muscle cells and increased thrombogenesis and expressed in disease states such as, for instance: coronary heart disease, peripheral artery disease, intermittent claudication, thrombosis, restenosis after angioplasty, extra-cranial carotid atherosclerosis, stroke and atherosclerosis occurring after heart transplant.

Furthermore, the compounds of the present invention have been found to have potent cholesterol lowering properties. Thus, studies performed in Cynomolgus monkeys have shown that the compounds of the present invention decrease total plasma cholesterol, in particular LDL (Low Density Lipoprotein) cholesterol. It is now well established that a high level of LDL cholesterol is a major risk factor of the atherosclerotic diseases. In addition, the compounds of the present invention were also shown in the same studies in Cynomolgus monkeys to decrease the levels of apoprotein B (apo B) which is the main protein of LDL and also its main ligand for LDL receptors. The mechanism of this decrease in apo B and in apo B-associated LDL does not involve the inhibition of cholesterol synthesis which is the mechanism demonstrated for the statins. Therefore, compounds of the present invention are useful for lowering cholesterol in patients who are resistant to treatment with a statin, and, conversely, also have a synergistic effect for lowering cholesterol in those patients who are responding to treatment with a statin.

Thus, compounds of the present invention are of use in therapy as cholesterol lowering agents. Furthermore, because of their dual profile in lowering plasma Lp(a) and plasma cholesterol, compounds of formula (I) are of use in therapy for the prevention and/or treatment of both the acute and chronic aspects of atherosclerosis.

Compounds of the present invention may also be of use in preventing and/or treating the above-mentioned disease states in combination with anti-hyperlipidaemic, anti-atherosclerotic, anti-diabetic, anti-anginal, anti-inflammatory or anti-hypertension agents. Examples of the above include cholesterol synthesis inhibitors such as statins, for instance atorvastatin, simvastatin, pravastatin, cerivastatin, fluvastatin, lovastatin and ZD 4522 (also referred to as S-4522, Astra Zeneca), anti-oxidants such as probucol, insulin sensitisers such as a PPAR gamma activator, for instance G1262570 (Glaxo Wellcome) and the glitazone class of compounds such as rosiglitazone (Avandia, SmithKline Beecham), troglitazone and pioglitazone, calcium channel antagonists, and anti-inflammatory drugs such as NSAIDs.

For therapeutic use, the compounds of the present invention will generally be administered in a standard pharmaceutical composition. Accordingly in a further aspect, the invention provides for a pharmaceutical composition comprising a compound of formula (I) and a pharmaceutically acceptable excipient or carrier. Suitable excipients and carriers are well known in the art and will be selected with regard to the intended route of administration and standard pharmaceutical practice. For example, the compositions may be administered orally in the form of tablets containing such excipients as starch or lactose, or in capsules, ovules or lozenges either alone or in admixture with excipients, or in the form of elixirs or suspensions containing flavoring or coloring agents. They may be injected parenterally, for example, intravenously, intramuscularly or subcutaneously. For parenteral administration, they are best used in the form of a sterile aqueous solution that may contain other substances, for example, enough salts or glucose to make the solution isotonic with blood. The choice of form for administration as well as effective dosages will vary depending, inter alia, on the condition being treated. The choice of mode of administration and dosage is within the skill of the art.

The compounds of formula (I) and their pharmaceutically acceptable salts which are active when given orally can be formulated as liquids, for example syrups, suspensions or emulsions or as solids for example, tablets, capsules and lozenges. A liquid formulation will generally consist of a suspension or solution of the compound or pharmaceutically acceptable salt in suitable liquid carrier(s) for example, ethanol, glycerine, non-aqueous solvent, for example polyethylene glycol, oils, or water with a suspending agent, preservative, flavoring or coloring agents. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats. Preferably the composition is in unit dose form such as a tablet or capsule.

Each dosage unit for oral administration contains preferably from 1 to 250 mg (and for parenteral administration contains preferably from 0.1 to 25 mg) of a compound of formula (I) or a pharmaceutically acceptable salt thereof calculated as the free base.

The pharmaceutically acceptable compounds of the invention will normally be administered to a subject in a daily dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of formula (I) or a pharmaceutically acceptable salt thereof calculated as the free base, the compound being administered 1 to 4 times per day.

The invention also relates to a process for preparing novel β-substituted-β-aminoethylphosphonate derivatives of formula (I) which is described below.

Compounds of formula (I) in which $Z^0$ is hydrogen may be prepared by a process which comprises treating an imine of formula (II):

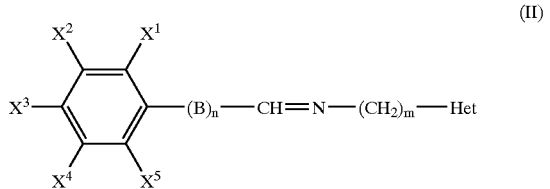

in which Het, $X^1$, $X^2$, $X^3$, $X^4$, $X^5$, B, n and m are as previously defined; with the anion of a substituted dialkyl methylphosphonate of formula (III):

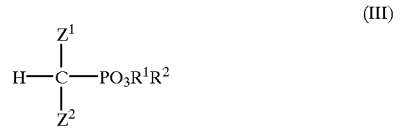

in which $Z^1$, $Z^2$, $R^1$ and $R^2$ are as previously defined; formed in situ by the treatment of compound (III) with a suitable strong base, for instance n-butyl lithium or lithium di-isopropylamide.

The reaction may be carried out in a solvent. Suitable solvents include diethyl ether, tetrahydrofuran (THF), 1,2-dimethoxyethane; the preferred solvent is THF. Suitable reaction temperatures are in the range of −78° C. to 25° C., the preferred reaction temperature is between −78° C. and −20° C. Suitable reaction times are between 30 min and 6 h, the preferred reaction times are between 1 h and 3 h, whereupon the reaction is stopped by hydrolysis and worked up according to standard methods in organic synthesis.

Such an imine compound of formula (II) may be obtained by condensing an aldehyde compound of formula (IV):

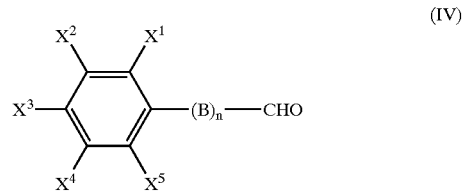

in which $X^1$, $X^2$, $X^3$, $X^4$, $X^5$, B and n are as previously defined; with a primary amine of formula (V):

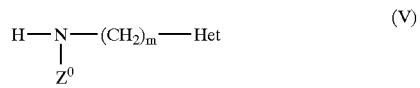

in which Het, $Z^0$ and m are as previously described; under imine forming conditions. Suitably, the condensation may be effected with or without a catalyst in a solvent such as ether, tetrahydrofuran, benzene, toluene or ethanol. Suitable catalysts include molecular sieve, magnesium sulphate, trialkyl orthoformate, an acid such as glacial acetic acid, p-toluenesulfonic acid, thionyl chloride, titanium tetrachloride, boron trifluoride etherate, or a base such as potassium carbonate. The reaction is suitably carried out in the range of 0° C. to the boiling point of the solvent being used. For less reactive amines or aldehydes, the reaction may be usefully carried out by heating to reflux a toluene mixture of equimolar amounts of an aldehyde of formula (IV) and an amine of formula (V), with concomitant elimination of water in a Dean-Stark apparatus.

When the imine of formula (II) comprises substituents that may react under the strongly alkaline reaction conditions employed and cause troublesome side reactions, i.e. when any of the substituents $X^1$, $X^2$, $X^3$, $X^4$, $X^5$ is a hydroxy group, then such a substituent needs to be protected. A particularly effective way of protecting the OH group is to convert it into an alkyl silyl ether, such as trimethyl silyl ether ($Me_3Si$ ether or Tms ether) or a t-butyldimethyl silyl ether ($tBuMe_2Si$ ether or Tbs ether). An integral part of this invention is the conversion of an imine of formula (II) comprising a hydroxy group into the corresponding Tbs ether. Suitable protection reaction conditions are the use of t-butyldimethylsilyl chloride in presence of imidazole in dimethylformamide. Such an Tbs protected imine then undergoes a selective addition of the dialkyl methylphosphonate of formula (III) under strongly alkaline conditions to form a Tbs protected β-substituted-β-aminophosphonate. The Tbs protecting group can then be cleaved by fluoride reagents well established in the art. Suitable deprotection reaction conditions involve reacting the Tbs protected compound with tetrabutyl ammonium fluoride in glacial acetic acid. The Tbs protected imine can be prepared by two alternatives: (1) protection of the OH substituent of the imine prepared by conventional methods described above; or (2) protection of the OH substituent of the aldehyde prior to formation of the imine.

The invention is further described in the following examples which are intended to illustrate the invention without limiting its scope. The abbreviations used in this application are the following: in the tables, n is normal, i is iso, s is secondary and t is tertiary; in the description of the NMR spectra, respectively s is singlet, d doublet, t triplet q quadruplet and m multiplet; and TsOH is p-toluenesulfonic acid monohydrate.

The temperatures were recorded in degrees Celsius and the melting points are not corrected. The identity of the compounds prepared in the following examples was established by their infrared (IR), mass (MS) and nuclear magnetic resonance (NMR) spectra. The purity of the compounds was checked by thin layer, gas liquid or high performance liquid chromatographies.

EXAMPLES OF THE INVENTION

Example 1

Diethyl β-(3,5-dimethoxy-4-hydroxyphenyl)-β-[N-(3-pyridyl)-amino]-ethylphosphonate

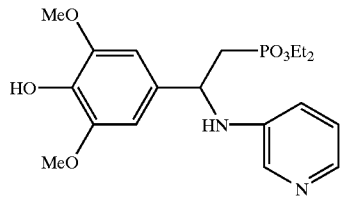

Imidazole (14.8 g, 217.6 mmol) was added portionwise to a well stirred mixture of syringaldehyde (12.0 g, 65.83 mmol) and t-butyldimethylsilyl chloride (14.9 g, 98.9 mmol) in 80 ml N,N-dimethylformamide (DMF) and stirring was continued for 3 h at room temperature. The mixture was poured into water kept at 0° C. to which was added a 25% ammonium hydroxide solution until pH 7 was reached. The aqueous phase was extracted with dichloromethane, the organic phase was dried over $MgSO_4$. Evaporation of the solvent gave an oil which was purified by column chromatography (silica gel, eluent: $CH_2Cl_2$). The pure fractions gave 16.4 g (84%) of a solid, mp=74–76° C.

A mixture of 10.6 g (35.8 mmol) of 4-(t-butyldimethylsilyloxy)-3,5-dimethoxybenzaldehyde, 3.36 g (35.8 mmol) of 3-aminopyridine and a catalytic amount of p-toluenesulfonic acid (ca. 5 mg) dissolved in 80 ml toluene contained in a flask connected to a Dean Stark apparatus was refluxed for 4 h. The solution was evaporated to dryness to give 12.5 g (94%) of the crude imine.

N-butyllithium (36.9 ml of a 1.6 M solution in hexane, 59.14 mmol) was added dropwise to 100 ml of dry THF kept at −78° C. Diethyl methylphosphonate (9.0 g, 59.14 mmol) was added, the mixture was stirred for 15 min at −78° C. then a solution of N-(3-pyridyl) 4-(t-butyldimethylsilyloxy)-3,5-dimethoxybenzaldimine (11.0 g, 29.57 mmol) in 15 ml dry THF was added dropwise and the resulting mixture was stirred at −78° C. for 1 h. A GLC check of a reaction sample showed that the imine has reacted completely; the reaction temperature was left to reach −30° C. then hydrolysis was carried out with a saturated ammonium chloride solution. The quenched reaction mixture was extracted with diethyl ether, the ether extract was dried over $MgSO_4$, filtered and evaporated to dryness. The residue was purified by column chromatography (silica gel, 9/1 $CH_2Cl_2$/MeOH) to give 11.6 g (75%) of diethyl β-(4-t-butyldimethylsilyloxy-3,5-dimethoxyphenyl)-β-[N-(3-pyridyl)-amino]-ethylphosphonate as a brown oil.

The previous compound (11.6 g, 22.18 mmol) and tetrabutylammonium fluoride trihydrate (TBAF) (27.94 g, 88.7 mmol) were placed in 80 ml THF to which were added dropwise 15.97 g (266.1 mmol) glacial acetic acid. After stirring at 20° C. for 3 h a GLC test showed that the Tbs protected compound has entirely reacted. The reaction mixture was extracted with dichloromethane, the organic phase was washed with a saturated bicarbonate solution, dried over $MgSO_4$. The residue of the evaporated extract was purified by column chromatography (silica gel, 9/1 $CH_2Cl_2$/MeOH). The pure fractions were recrystallized from a mixture of petroleum ether/$CH_2Cl_2$ to give 2.85 g (31%) of the title compound as a white solid, mp=164–166° C.

MS (m/e)=410: $M^+$, 316 (100%): $M^+$—$C_5H_4N$—$NH_2$, 259: $M^+$—$CH_2PO_3Et_2$, 94: $C_5H_4N$—$NH_2$ NMR ($CDCl_3$): δ=8.01, 7.94, 6.98 and 6.74 (4m, 1H each): aromatic H, 3-pyridyl 6.62 (s, 2H): aromatic H, substituted phenyl 5.3 (s, 1H): O$\underline{H}$ 5.27 (d, 1H, J=3 Hz): N—H 4.57–4.51 (m, 1H): C$\underline{H}$—$CH_2$—$PO_3Et_2$ 4.13–4.03 (m, 4H): P—O—$C\underline{H}_2$—$CH_3$ 3.85 (s, 6H): Ph-O$CH_3$ 2.25 (dxd, J=7 and 17 Hz, 2H): CH—$C\underline{H}_2$—$PO_3Et_2$ 1.29 and 1.28 (2t, J=7 Hz): P—O—$CH_2$—$CH_3$

Example 2

Diethyl β-(4-hydroxy-3-methoxy-5-methylphenyl)-β-[N-(3-pyridyl)-amino]-ethylphosphonate

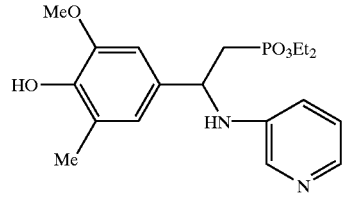

A mixture of 35.0 g (0.21 mol) of 4-hydroxy-3-methoxy-5-methylbenzaldehyde (mp=98–100°), 19.8 g (0.21 mmol) of 3-aminopyridine and a catalytic amount of p-toluenesulfonic acid (ca. 10 mg) dissolved in 150 ml toluene contained in a flask connected to a Dean Stark apparatus was refluxed for 6 h. The quantitative formation of the Schiff's base was indicated by the formation of an equivalent amount of water. The toluene solution was evaporated to dryness to give 51 g (100%) of the crude imine. To a DMT solution (300 ml) of this material and t-butyldimethylsilyl chloride (47.6 g, 0.32 mol) was added imidazole (28.7 g, 0.42 mol) in three portions and the resulting mixture was stirred at room temperature for 6 h. The mixture was poured into ice water, neutralized by a 25% aqueous solution of ammonia and finally extracted with $CH_2Cl_2$. The organic phase was dried ($MgSO_4$), filtered and evaporated under vacuum to remove the last traces of DMF until constant weight. The Tbs protected imine was obtained as a brown oil (75 g, 99%) and was directly used in the next step.

To 800 ml of dry THF placed in a 2 l two-necked flask were added n-butyllithium (263 ml of a 1.6 M solution in hexane, 0.42 mol) and the resulting solution was stirred at −78° C. for 15 min. After the addition of diethyl methylphosphonate (64.0 g, 0.42 mol) the mixture was stirred for 15 min at −78° C. then a THF solution of N-(3-pyridyl) 4-(t-butyldimethylsilyloxy)-3-methoxy-5-methylbenzaldimine (75.0 g, 0.21 mol) was added dropwise and the resulting mixture was stirred at −78° C. for 90 min. After a GLC check of a reaction sample has showed that the imine has reacted completely, hydrolysis was carried out with a saturated ammonium chloride solution. The quenched reaction mixture was extracted with diethyl ether, the dried ether extract (MgSO$_4$) was filtered and evaporated to dryness to give 122 g of a brown oil. Column chromatography (silica gel, 9/1 CH$_2$Cl$_2$/MeOH) gave 90.5 g (86%) of a light-brown oil.

Glacial acetic acid (130 ml) was added to 500 ml of a THF solution containing a mixture of diethyl β-(4-t-butyldimethylsilyloxy-3-methoxy-5-methylphenyl)-β-[N-(3-pyridyl)-amino]-ethylphosphonate (90.5 g, 0.18 mol) and tetrabutylammonium fluoride trihydrate (TBAF) (224.5 g, 0.71 mol). After stirring at 20° C. for 3 h a GLC test showed that the Tbs protected compound has entirely reacted. The reaction mixture was extracted with dichloromethane, the organic phase was washed with a saturated bicarbonate solution, dried over MgSO$_4$ and evaporated. Purification by column chromatography (silica gel, 9/1 CH$_2$Cl$_2$/MeOH) gave 53 g of pure fractions. Recrystallization from a mixture of petroleum ether/CH$_2$Cl$_2$ gave 27 g (39%) of the title compound as a white solid, mp=156–158° C.

MS (m/e)=394: M$^+$, 300: M$^+$—C$_5$H$_4$N—NH$_2$, 243: M$^+$—CH$_2$PO$_3$Et$_2$, 94 (100%): C$_5$H$_4$N—NH$_2$ NMR (CDCl$_3$): δ=8.00, 7.92, 6.97 and 6.76 (4m, 1H each): aromatic H, 3-pyridyl 6.75 (m, 2H): aromatic H, substituted phenyl 5.75 (broad, 1H): OH 5.21 (d, 1H, J=3 Hz): N—H 4.57–4.49 (m, 1H): CH—CH$_2$—PO$_3$Et$_2$ 4.12–4.0 (m, 4H): P—O—CH$_2$—CH$_3$ 3.82 (s, 3H): Ph-OCH$_3$ 2.24 (dxd, J=7 and 17 Hz, 2H): CH—CH$_2$—PO$_3$Et$_2$ 2.22 (s, 3H): Ph-CH$_3$ 1.28 (dxt, J=1 and 7 Hz): P—O—CH$_2$—CH$_3$ Example 3

Dimethyl β-(4-hydroxy-3-methoxy-5-methylphenyl)-β-[N-(3-(2,6-dimethyl)pyridyl))-amino]-ethylphosphonate

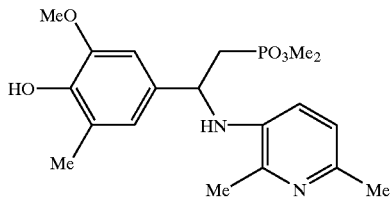

A mixture of 4-hydroxy-3-methoxy-5-methylbenzaldehyde (15.0 g, 90.4 mmol), 3-amino-2,6-dimethylpyridine (11.0 g, 90.36 mmol) and 5 mg TsOH dissolved in 150 ml toluene connected to a Dean Stark apparatus was refluxed for 7 h. Toluene was evaporated to dryness to give 24.4 g (100%) of an orange oil which was used directly for the next step. To a DMF solution (150 ml) of this material (24.4 g, 90.4 mmol) and t-butyldimethylsilyl chloride (20.4 g, 135.6 mmol) was added imidazole (12.3 g, 180.7 mmol) and the resulting mixture was stirred at room temperature for 6 h. The mixture was poured into ice-water, neutralized by a 25% aqueous solution of ammonia and finally extracted with CH$_2$Cl$_2$. Evaporation of the dried solvent gave the crude Tbs protected imine as a brown oil (28 g, 81%).

To 120 ml of dry THF was added n-butyllithium (39 ml of a 1.6 M solution in hexane, 62.5 mmol) and the resulting solution was stirred at −78° C. for 15 min. After the addition of dimethyl methylphosphonate (7.75 g, 62.5 mmol) the mixture was stirred for 15 min at −78° C. then N-[3-(2,6-dimethylpyridyl)]4-(t-butyldimethylsilyloxy)-3-methoxy-5-methylbenzaldimine (12.0 g, 31.3 mmol) was added dropwise and the resulting mixture was stirred at −78° C. for 1 h. Hydrolysis was carried out with a saturated ammonium chloride solution and the quenched reaction mixture was extracted with diethyl ether. Column chromatography of the ether extracts (silica gel, 95/5 CH$_2$Cl$_2$/MeOH) gave 5.5 g (35%) of a light-brown oil.

Glacial acetic acid (7.8 g) was added to 40 ml of a THF solution containing a mixture of dimethyl β-(4-t-butyldimethylsilyloxy-3-methoxy-5-methylphenyl)-β-[N-[(3-(2,6-dimethylpyridyl)]-amino]-ethylphosphonate (5.5 g, 10.83 mmol) and tetrabutylammonium fluoride trihydrate (TBAF) (13.6 g, 43.31 mmol). After stirring for 3 h at 20° C. the reaction mixture was extracted with dichloromethane, the organic phase was washed (NaHCO$_3$), dried (MgSO$_4$) and evaporated. Purification by column chromatography (silicagel, 9/1 CH$_2$Cl$_2$/MeOH) gave 2.9 g (24%) of the title compound as a yellow solid.

MS (m/e)=394: M$^+$, 272: M$^+$+1—C$_7$H$_8$N—NH$_2$, 259: M$^+$—CH$_2$PO$_3$Me$_2$, 122 (100%): C$_7$H$_8$N—NH$_2$ NMR (CDCl$_3$): δ=6.73 (m, 2H): aromatic H, substituted phenyl 6.69 and 6.49 (2d, J=8.5 Hz, 2H): aromatic H, 3-pyridyl 5.65 (broad s, 1H): OH 5.03 (m, 1H, J=2 Hz): N—H 4.56–4.48 (m, 1H): CH—CH$_2$—PO$_3$Me$_2$ 3.82 (s, 3H): Ph-OCH$_3$ 3.72 and 3.69 (2d, J=6.5 Hz, 4H): P—O—CH$_3$ 2.54 and 2.37 (2s, 6H total): Py-CH$_3$ 2.32–2.24 (m, 2H): CH—CH$_2$—PO$_3$Et$_2$ 2.23 (1s, sH): Ph-CH$_3$ Example 4

Diethyl β-(4-hydroxy-3-methoxy-5-methylphenyl)-β-[N-(3-(2,6-dimethyl)pyridyl))-amino]-ethylphosphonate

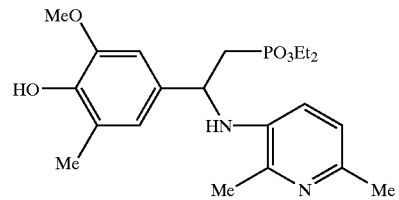

To 800 ml of dry TBF placed in a 2 l two-necked flask were added n-butyllithium (283 ml of a 1.6 M solution in hexane, 0.45 mol) and the resulting solution was stirred at −78° C. for 15 min. After the addition of diethyl methylphosphonate (68.9 g, 0.45 mol) the mixture was stirred for 15 min at −78° C. then a TEEF solution of N-[3-(2,6-dimethylpyridyl]4-(t-butyldimethylsilyloxy)-3-methoxy-5-methylbenzaldimine (87.0 g, 0.23 mol) was added dropwise and the resulting mixture was stirred at −78° C. for 90 min. After verification that the imine has reacted completely (GLC analysis), hydrolysis was carried out with a saturated ammonium chloride solution. The quenched reaction mixture was extracted with diethyl ether, the dried ether extract (MgSO$_4$) was filtered and evaporated to dryness. Purification by column chromatography (silica gel, 95/5 CH$_2$Cl$_2$/MeOH) gave 102.8 g (85%) of a light-brown oil.

Glacial acetic acid (138 g, 2.3 mol) was added to 500 ml of a TBF solution containing a mixture of diethyl β-(4-t-butyldimethylsilyloxy-3-methoxy-5-methylphenyl)-β-[N-[(3-(2,6-dimethylpyridyl)]-amino]-ethylphosphonate (102.8 g, 0.19 mol) and tetrabutylammonium fluoride trihydrate (TBAF) (241.6 g, 0.77 mol). After stirring at 20° C. for 3 h a GLC test showed that the Tbs protected compound has entirely reacted. The reaction mixture was extracted with dichloromethane, the organic phase was washed (NaHCO$_3$), dried (MgSO$_4$) and evaporated. Purification by column chromatography (silica gel, 9/1 CH$_2$Cl$_2$/MeOH) gave after recrystallization from a mixture of petroleum ether/CH$_2$Cl$_2$ 31 g (45%) of the title compound as a light yellow solid, mp=89–91° C.

MS (m/e)=422: M$^+$, 300: M$^+$—C$_7$H$_8$N—NH$_2$, 122 (100%): C$_7$H$_8$N—NH$_2$ NMR (CDCl$_3$): δ=6.73 (m, 2H): aromatic H, substituted phenyl 6.69 and 6.48 (2d, J=8 Hz, 2H): aromatic H, 3-pyridyl 5.68 (broad, 1H): OH 5.10 (d, 1H, J=2 Hz): N—H 4.55–4.47 (m, 1H): CH—CH$_2$—PO$_3$Et$_2$ 4.15–4.03 (m, 4H): P—O—CH$_2$—CH$_3$ 3.82 (s, 3H): Ph—OCH$_3$ 2.54 and 2.37 (2s, 6H total): Py-CH$_3$ 2.30–2.23 (m, 2H): CH—CH$_2$—PO$_3$Et$_2$ 2.23 (is, 3H): Ph-CH$_3$ 1.28 and 1.27 (2t, J=7 Hz, 6H total): P—O—CH$_2$—CH$_3$ Example 5

Diisopropyl β-(4-hydroxy-3-methoxy-5-methylphenyl)-β-[N-(3-(2,6-dimethyl)pyridyl))-amino]-ethylphosphonate

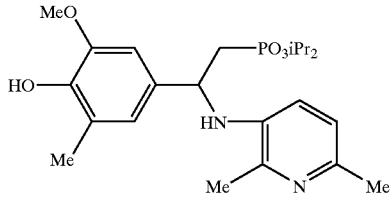

N-[3-(2,6-dimethylpyridyl]4-(t-butyldimethylsilyloxy)-3-methoxy-5-methylbenzaldimine (10.0 g, 26.0 mol) was reacted with n-butyllithium (32.6 ml of a 1.6M hexane solution, 52.1 mmol) and diisopropyl methylphosphonate (9.4 g, 52.1 mmol) and the compound obtained, diisopropyl β-(4-t-butyldimethylsilyloxy-3-methoxy-5-methylphenyl)-β-[N-[3-(2,6-dimethyl-pyridyl)-amino]]-ethylphosphonate (5.5 g, 9.8 mmol) was deprotected by reaction with tetrabutylammonium fluoride trihydrate (TBAF) (12.3 g, 39 mmol) and acetic acid (7.0 g, 117 mmol) exactly as described in Example 4 to give 2.25 g of the title compound, mp=81–83° C. (petroleum ether/CH$_2$Cl$_2$).

MS (m/e)=450: M$^+$, 328: M$^+$—C$_7$H$_8$N—NH$_2$, 122: C$_7$H$_8$N—NH$_2$ NMR (CDCl$_3$): δ=6.73 (m, 2H): aromatic H, substituted phenyl 6.68 and 6.46 (2d, J=8 Hz, 2H): aromatic H, 3-pyridyl 5.65 (broad, 1H): OH 5.22 (m, 1H, J=2 Hz): N—H 4.75–4.65 (m, 2H): P—O—CH—(CH$_3$)$_2$ 4.50–4.42 (m, 1H): CH—CH$_2$—PO$_3$iPr$_2$ 3.82 (s, 3H): Ph-OCH$_3$ 2.56 and 2.37 (2s, 6H total): Py-CH$_3$ 2.25–2.17 (m, 2H): CH—CH$_2$—PO$_3$iPr$_2$ 2.23 (1s, 3H): Ph-CH$_3$ 1.32, 1.30, 1.26 and 1.19 (4d, J=7 Hz, 12H total): P—O—CH—(CH$_3$)$_2$ Example 6

Diethyl β-(3,4,5-trimethoxyphenyl)-β-[N-(3-pyridyl)-amino]-ethylphosphonate

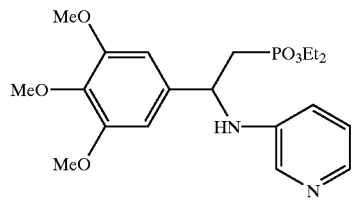

A mixture of 3,4,5-trimethoxybenzaldehyde (10.2 g, 52 mmol), 3-aminopyridine (4.9 g, 52 mmol) and a catalytic amount of TsOH in 50 ml toluene was refluxed for 16 h in a flask connected to a Dean-Stark trap. Evaporation of toluene gave 14 g (99%) of the corresponding imine, mp=69–71° C., which was used directly in the next step.

N-butyllithium (32 ml of a 1.6 M solution in hexane, 51.5 mmol) was added dropwise to 80 ml of dry THF kept at −78° C. Diethyl methylphosphonate (7.80 g, 51.5 mmol) was added, the mixture was stirred for 15 min at −78° C. then a solution of N-(3-pyridyl) 3,4,5-trimethoxybenzaldimine (7.0 g, 25.7 mmol) in 10 ml dry THF was added dropwise and the resulting mixture was stirred at −78° C. for 1 h. The reaction mixture quenched with a saturated NH$_4$Cl solution was extracted with diethyl ether, the ether extract was dried (MgSO$_4$), filtered and evaporated. The residue was purified by column chromatography (silica gel, 9/1 CH$_2$Cl$_2$/MeOH) to give 6.2 g (57%) of the title compound, mp=104–106° C.

MS (m/e)=424: M$^+$, 331 (100%): M$^+$—C$_5$H$_4$N—NH NMR (CDCl$_3$): δ=7.99, 7.94, 7.0 and 6.76 (4m, 1H each): aromatic H, 3-pyridyl 6.61 (s, 2H): aromatic H, substituted phenyl 5.30 (m, 1H): N—H 4.60–4.53 (m, 1H): CH—CH$_2$—PO$_3$Et$_2$ 4.14–4.03 (m, 4H): P—O—CH$_2$—CH$_3$ 3.83 and 3.82 (3s, 9H total): Ph-OCH$_3$ 2.26 (distorted dxd, J=7 and 17 Hz, 2H): CH—CH$_2$—PO$_3$Et$_2$ 1.29 and 1.28 (2t, J=7 Hz): P—O—CH$_2$—CH$_3$ Example 7

Diethyl β-(4,5-dimethoxy-3-hydroxyphenyl)-β-[N-(3-(2,6-dimethylpyridyl))-amino]-ethylphosphonate

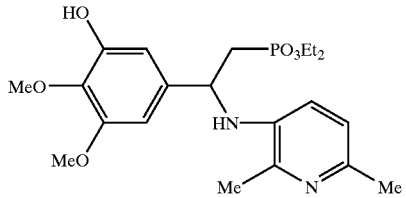

A mixture of 4,5-dimethoxy-3-hydroxybenzaldehyde (9.6 g, 52.9 mmol), 3-amino-2,6-dimethylpyridine (6.45 g, 52.9 mmol) dissolved in 150 ml toluene and 5 mg of TsOH contained in a flask connected to a Dean Stark apparatus was refluxed for 16 h. The solution was evaporated to dryness to give 15.1 g (100%) of a solid which was used directly for the next step. To a DMF solution (85 ml) of this material (15.1 g, 52.9 mmol) and t-butyldimethylsilyl chloride (11.93 g, 79 mmol) was added imidazole (7.2 g, 105.7 mmol) and the resulting mixture was stirred at room temperature for 6 h. The mixture was poured into ice-water, neutralized by a 25% aqueous solution of ammonia and finally extracted with CH₂Cl₂. Evaporation of the dried solvent gave the crude Tbs protected imine as a brown oil (21.2 g, 100%).

To 90 ml of dry TBF placed in a two-necked flask were added n-butyllithium (31 ml of a 1.6 M solution in hexane, 50 mmol) and the resulting solution was stirred at −78° C. for 15 min. After the addition of diethyl methylphosphonate (7.6 g, 50 mmol) the mixture was stirred for 15 min at −78° C. then a TBF solution of N-[3-(2,6-dimethylpyridyl)]3-(t-butyldimethylsilyloxy)-4,5-dimethoxybenzaldimine (10.0 g, 25 mmol) was added dropwise and the resulting mixture was stirred at −78° C. for 90 min. The quenched reaction mixture (NH₄Cl solution) was extracted with diethyl ether, the dried ether extract (MgSO₄) was filtered and evaporated to give 14.5 g (103%) of the crude material as a brown oil. Glacial acetic acid (19 g, 315 mmol) was added to 70 ml of a THF solution containing a mixture of diethyl β-(3-t-butyldimethylsilyloxy-4,5-dimethoxyphenyl)-β-[N-[(3-(2,6-dimethylpyridyl)]-amino]-ethylphosphonate (14.5 g, 26.3 mmol) and tetrabutylammonium fluoride trihydrate (TBAF) (33.1 g, 105 mmol). After stirring at 20° C. for 3 h the reaction mixture was extracted with dichloromethane, the organic phase was washed (NaHCO₃), dried (MgSO₄) and evaporated. Purification by column chromatography (silica gel, 9/1 CH₂Cl₂/MeOH) gave after recrystallization from a mixture of petroleum ether/CH₂Cl₂ the title compound (3.2 g, 29%) as a light yellow solid, mp=121–123° C.

MS (m/e)=438: M⁺, 317: M⁺—C₇H₈N—NH, 287: M⁺—CH₂—PO₃Et₂, 122 (100%): C₇H₈N—NH₂ NMR (CDCl₃): δ=7.4 (broad peak, 1H): O<u>H</u> 6.70 and 6.44 (2d, J=8.5 Hz, 2H): aromatic H, 3-pyridyl 6.61 and 6.46 (2m, 2H total): aromatic H, substituted phenyl 5.11 (m, 1H): N—H 4.55–4.46 (m, 1H): C<u>H</u>—CH₂—PO₃Et₂ 4.12–4.01 (m, 4H): P—O—C<u>H</u>₂—CH₃ 3.88 and 3.83 (2s, 6H total): Ph-OC<u>H</u>₃ 2.41 and 2.37 (2s, 9H total): Py-C<u>H</u>₃ 2.31–2.24 (m, 2H): CH—C<u>H</u>₂—PO₃Et₂ 1.27 (t, J=7 Hz, 6H total): P—O—CH₂—C<u>H</u>₃

Example 8

Diethyl β-(3-hydroxy-4-methoxy-5-methylphenyl)-β-[N-(3-(2,6-dimethylpyridyl))-amino]-ethylphosphonate

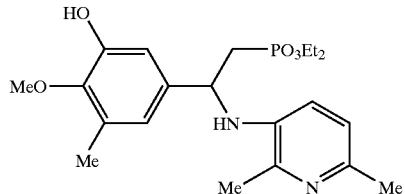

A mixture of 3-hydroxy-4-methoxy-5-methylbenzaldehyde (12 g, 72.3 mmol), 3-amino-2,6-dimethylpyridine (8.82 g, 72.3 mmol) dissolved in 160 ml toluene and 5 mg of TsOH contained in a flask connected to a Dean Stark apparatus was refluxed for 12 h. Toluene was evaporated to give 19.5 g (100%) of an oil which was used directly for the next step. To a DMF solution (85 ml) of this material (19.5 g, 72.3 mmol) and t-butyldimethylsilyl chloride (16.3 g, 108.4 mmol) was added imidazole (9.8 g, 144.6 mmol) and the resulting mixture was stirred at room temperature for 6 h. The mixture was poured into ice-water, neutralized by a 25% aqueous solution of ammonia and finally extracted with CH₂Cl₂. Evaporation of the dried solvent gave the crude Tbs protected imine as a brown oil (27.8 g, 100%).

To 120 ml of dry THF placed in a two-necked flask were added n-butyllithium (42 ml of a 1.6 M solution in hexane, 72.4 mmol) and the resulting solution was stirred at −78° C. for 15 min. After the addition of diethyl methylphosphonate (11 g, 72.4 mmol) the mixture was stirred for 15 min at −78° C. then a THF solution of N-[3-(2,6-dimethylpyridyl)] 3-(t-butyldimethylsilyloxy)-4-methoxy-5-methylbenzaldimine (13.9 g, 36.2 mmol) was added dropwise and the resulting mixture was stirred at −78° C. for 90 min. The quenched reaction mixture (NH₄Cl solution) was extracted with diethyl ether, the dried ether extract was submitted to column chromatography (silica gel, 9/1 CH₂Cl₂/MeOH to give 18.0 g (93%) of a brown oil. Glacial acetic acid (24 g, 403 mmol) was added to 90 ml of a THF solution containing a mixture of diethyl β-(3-t-butyldimethylsilyloxy-4-methoxy-5-methylphenyl)-β-[N-[(3-(2,6-dimethylpyridyl)]-amino]-ethylphosphonate (18 g, 33.6 mmol) and tetrabutylammonium fluoride trihydrate (TBAF) (42 g, 134 mmol). After stirring at 20° C. for 3 h the reaction mixture was extracted with dichloromethane, the organic phase was washed (NaHCO₃), dried (MgSO₄) and evaporated. Purification by column chromatography (silica gel, 9/1 CH₂Cl₂/MeOH) gave after recrystallization from a mixture of petroleum ether/CH₂Cl₂ the title compound (3.6 g, 24%) as a light yellow solid, mp=128–130° C.

MS (m/e)=422: M⁺, 301: M⁺—C₇H₈N—NH, 271: M⁺—CH₂—PO₃Et₂, 122 (100): C₇H₈N—NH₂ NMR (CDCl₃): δ=8.0 (broad peak, 1H): O<u>H</u> 6.77 and 6.62 (2m, 2H total): aromatic H, substituted phenyl 6.69 and 6.44 (2d, J=8.5 Hz, 2H): aromatic H, 3-pyridyl 5.09 (d, 1H, J=3 Hz): N—H 4.55–4.47 (m, 1H): C<u>H</u>—CH₂—PO₃Et₂ 4.10–3.95 (m, 4H): P—O—C<u>H</u>₂—CH₃ 3.81 (s, 3H): Ph-OC<u>H</u>₃ 2.36 and 2.28 (3s, 9H total): Py-C<u>H</u>₃ and Ph-C<u>H</u>₃ 2.30–2.23 (m, 2H): CH—C<u>H</u>₂—PO₃Et₂ 1.24: (2t, J=7 Hz, 6H total): P—O—CH₂—C<u>H</u>₃

Example 9

Diethyl β-(4-hydroxy-3-methoxy-5-methylphenyl)-β-[N-(3-(2,6-dimethyl)pyridyl))-amino]-(α-methylethylphosphonate

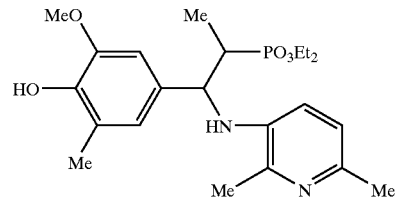

To 50 ml of dry THF placed in a two-necked flask were added n-butyllithium (19.5 ml of a 1.6 M solution in hexane, 31.3 mmol) and the resulting solution was stirred at −78° C. for 15 min. After the addition of diethyl ethylphosphonate (5.2 g, 31.3 mmol) the mixture was stirred for 15 min at −78° C. then a THF solution of N-[3-(2,6-dimethylpyridyl)]4-(t-butyldimethylsilyloxy)-3-methoxy-5-methylbenzaldimine (6.0 g, 15.6 mmol) was added dropwise and the resulting mixture was stirred at −78° C. for 90 min. The reaction mixture was quenched (NH₄Cl), extracted with diethyl ether, the dried ether extract (MgSO₄) was filtered and evaporated to dryness. Purification by column chromatography (silica gel, 95/5 CH₂Cl₂/MeOH) gave 3.9 g (46%) of a light-brown oil.

Glacial acetic acid (5.2 g, 86 mmol) was added to 20 ml of a THF solution containing a mixture of diethyl β-(4-t- butyldimethylsilyloxy-3-methoxy-5-methylphenyl)-β-[N-[(3-(2,6-dimethylpyridyl)]-amino]-α-methyl-ethylphosphonate (3.9 g, 7 mmol) and tetrabutylammonium fluoride trihydrate (TBAF) (9.0 g, 29 mmol). After stirring at 20° C. for 3 h the reaction mixture was extracted with dichloromethane, the organic phase was washed (NaHCO$_3$), dried (MgSO$_4$) and evaporated. Column chromatography (silica gel, 9/1 CH$_2$Cl$_2$/MeOH) gave after recrystallization from a mixture of ligroine/ethanol 1.6 g (24%) of the title compound as a white solid, mp=194–196° C.

MS (m/e)=436: M$^+$, 314: M$^+$—C$_7$H$_8$N—NH$_2$, 271: M$^+$—CH(CH$_3$)—PO$_3$Et$_2$, 122 (100%): C$_7$H$_8$N—NH$_2$ NMR (CDCl$_3$): δ=6.66 (m, 2H): aromatic H, substituted phenyl 6.65 and 6.37 (2d, J=8 Hz, 2H): aromatic H, 3-pyridyl 5.68 (broad, 1H): OH 4.97 (broad, 1H): N—H 4.64–4.57 (m, 1H): CH—CH(Me)—PO$_3$Et$_2$ 4.15–4.0 (m, 4H): P—O—CH$_2$—CH$_3$ 3.81 (s, 3H): Ph-OCH$_3$ 2.56 and 2.37 (2s, 6H total): Py-CH$_3$ 2.36–2.24 (m, 1H): CH—CH(Me)—PO$_3$Et$_2$ 2.23 (1s, 3H): Ph-CH$_3$ 1.29 and 1.26: (2t, J=7 Hz, 6H total): P—O—CH$_2$—CH$_3$ 1.15 (2d, J=7.5 and 17.5 Hz, 3H): CH—CH(Me)—PO$_3$Et$_2$ Example 10

Diethyl β-(4-hydroxy-3-methoxy-5-methylphenyl)-β-[N-(3-(2,6-dimethyl)pyridyl))-amino]-α,α-difluoro-ethylphosphonate

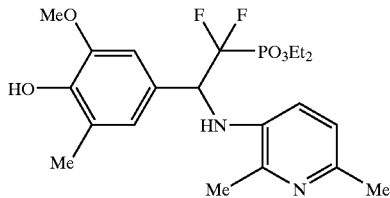

Throughout the whole reaction the temperature was kept at −78° C. To 150 ml of dry THF precooled to −78° C. were added in sequence with 15 min stirring time between each addition, n-butyllithium (25 ml of a 1.6 M solution in hexane, 40 mmol), diisopropyl amine (5.6 ml, 40 mmol), tetramethylethylenediamine (6.0 ml, 40 mmol), diethyl difluoromethylphosphonate (5 g, 27 mmol) and finally N-[3-(2,6-dimethylpyridyl)] 4-(t-butyldimethylsilyloxy)-3-methoxy-5-methyl benzaldimine (5.1 g, 13 mmol) and the resulting mixture was stirred at −78° C. for 1 h. Ater a GLC analysis has shown that the imine compound has completely reacted, the reaction mixture was quenched (NH$_4$Cl), extracted with diethyl ether, the dried ether extract (MgSO$_4$) was filtered and evaporated. Purification by column chromatography (silica gel, 95/5 CH$_2$Cl$_2$/MeOH) gave 5.5 g (73 %) of a light-brown oil.

Glacial acetic acid (7.0 g, 116 mmol) was added to 30 ml of a THF solution containing a mixture of diethyl β-(4-t-butyldimethylsilyloxy-3-methoxy-5-methylphenyl)-β-[N-[(3-(2,6-dimethylpyridyl)]-amino]-α,α-difluoro ethylphosphonate (5.5 g, 9.7 mmol) and tetrabutylammonium fluoride trihydrate (TBAF) (12.2 g, 39 mmol). After stirring at 20° C. for 3 h the reaction mixture was extracted with dichloromethane, the organic phase was washed (NaHCO$_3$), dried (MgSO$_4$) and evaporated. Column chromatography (silica gel, 9/1 CH$_2$Cl$_2$/MeOH) gave 0.32 g (7%) of the title compound as a brown oil.

MS (m/e)=458: M$^+$, 271 (100%): M$^+$—CF$_2$—PO$_3$Et$_2$ NMR (CDCl$_3$): δ=6.80 (m, 2H): aromatic H, substituted phenyl 6.74 and 6.60 (2d, J=8 Hz, 2H): aromatic H, 3-pyridyl 4.97 (d, J=2 Hz, 1H): N—H 4.83–4.73 (m, 1H): CH—CH$_2$-PO$_3$Et$_2$ 4.3–4.1 (m, 4H): P—O—CH$_2$—CH$_3$ 3.85 (s, 3H): Ph-OCH$_3$ 2.54 and 2.38 (2s, 6H total): Py-CH$_3$ 2.24 (1s, 3H): Ph-CH$_3$ 1.31 and 1.27 (2t, J=7 Hz, 6H total): P—O—CH$_2$—CH$_3$ Example 11

Diethyl β-(3,5-di-tert-butyl-4-methoxyphenyl)-β-[N-(3-pyridyl)-amino]-ethylphosphonate

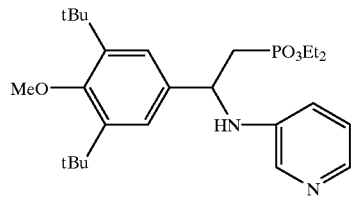

A mixture of 3,5-di-tert-butyl-4-methoxybenzaldehyde (4.5 g, 18.3 mmol), 3-aminopyridine (1.8 g, 19.5 mmol) and a catalytic amount of TsOH in 50 ml toluene was refluxed for 12 h in a flask connected to a Dean-Stark trap. Evaporation of toluene gave 5.8 g (98%) of the corresponding imine, which was used directly in the next step.

N-butyllithium (11.5 ml of a 1.6 M solution in hexane, 18.3 mmol) was added dropwise to 30 ml of dry THF kept at −78° C. Diethyl methylphosphonate (2.8 g, 18.3 mmol) was added, the mixture was stirred for 15 min at −78° C. then a solution of N-(3-pyridyl) 3,5-di-tert-butyl-4-methoxybenzaldimine (3.0 g, 9.2 mmol) in 5 ml dry TBF was added dropwise and the resulting mixture was stirred at −78° C. for 1 h. The reaction mixture quenched with a saturated NH$_4$Cl solution was extracted with diethyl ether, the ether extract was dried (MgSO$_4$), filtered and evaporated. The residue was purified by column chromatography (silica gel, 95/5 CH$_2$Cl$_2$/MeOH) to give 2.1 g (48%) of the title compound as an oil.

IR: cm$^{-1}$: 1290: P═O, 1050 and 1022: P—O—C.

Example 12

Diethyl β-(2,4-dimethyl-3-hydroxyphenyl)-β-[N-(5-(2-methylpyridyl))-amino]-ethylphosphonate

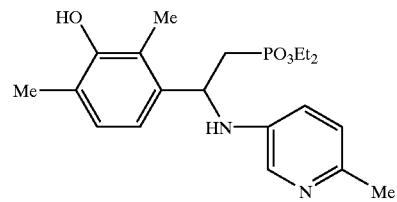

A mixture of 2,4-dimethyl-3-hydroxybenzaldehyde (3 g, 20.3 mmol), 5-amino-2-methylpyridine (2.1 g, 19.4 mmol) dissolved in 30 ml toluene and 5 mg of TsOH contained in a flask connected to a Dean Stark apparatus was refluxed for 4 h. Toluene was evaporated to give 4.8 g (100%) of an oil which was used directly for the next step. To a DMF solution (20 ml) of this material (4.8 g, 20 mmol) and t-butyldimethylsilyl chloride (4.5 g, 30.1 mmol) was added imidazole (2.72 g, 40 mmol) and the resulting mixture was stirred at room temperature for 6 h. The mixture was poured into ice-water, neutralized by a 25% aqueous solution of ammonia and finally extracted with CH$_2$Cl$_2$. Evaporation of the dried solvent gave the crude Tbs protected imine as a brown oil (6.1 g, 87%). To 60 ml of dry THF placed in a two-necked flask were added n-butyllithium (21 ml of a 1.6 M solution in hexane, 34.5 mmol) and the resulting solution was stirred at −78° C. for 15 min. After the addition of diethyl methylphosphonate (5.2 g, 34.6 mmol) the mixture was stirred for 15 min at −78° C. then a THF solution of the Tbs protected imine (6.13 g, 17.3 mmol) was added dropwise and the resulting mixture was stirred at −78° C. for 90 min. The quenched reaction mixture (NH$_4$Cl solution) was extracted with diethyl ether, the dried ether extract was submitted to column chromatography (silica gel, 9/1 CH$_2$Cl$_2$/MeOH to give 8.6 g (98%) of a brown oil. Glacial acetic acid (12 g, 204 mmol) was added to 40 ml of a THF solution containing a mixture of diethyl β-(2,4-dimethyl-3-t-butyldimethylsilyloxyphenyl)-β-(-[N-(5-(2-methylpyridyl))-amino]-ethylphosphonate (8.6 g, 17 mmol) and tetrabutylammonium fluoride trihydrate (TBAF) (21.4 g, 68 mmol). After stirring at 20° C. for 3 h the reaction mixture was extracted with dichloromethane, the organic phase was washed (NaHCO$_3$), dried (MgSO$_4$) and evaporated. Purification by column chromatography (silica gel, 9/1 CH$_2$Cl$_2$/MeOH) gave the title compound (0.7 g, 10%) as a light yellow oil.

MS (m/e)=392: M$^+$, 284: M$^+$—C$_6$H$_6$N—NH NMR (CDCl$_3$): δ=8.0 (broad peak, 1H): O$\underline{H}$ 7.75, 6.82 (2d, 2H) and 6.65 (d, 1H): aromatic H, 5-pyridyl 6.95 and 6.90 (2m, 2H): aromatic H, substituted phenyl 5.04 (d, 1H): N—H 4.85–4.75 (m, 1H): C$\underline{H}$—CH$_2$—PO$_3$Et$_2$ 4.15–4.05 (m, 4H): P—O—C$\underline{H}_2$—CH$_3$ 2.47(s, 3H): Py-C$\underline{H}_3$ 2.30 and 2.20 (2s, 6H): Ph-CH$_3$ 2.25–2.04 (m, 2H): CH—C$\underline{H}_2$—PO$_3$Et$_2$ 1.28 and 1.27: (2t, J=7 Hz, 6H total): P—O—CH$_2$—C$\underline{H}_3$ Example 13

Diethyl β-(3-hydroxy-5-methoxy-4-methylphenyl)-β-[N-(5-(2-methylpyridyl))-amino]-ethylphosphonate

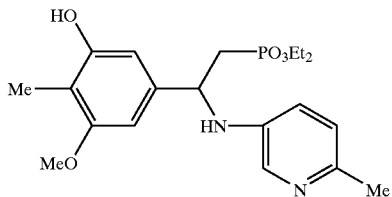

A mixture of 3-hydroxy-5-methoxy-4-methylbenzaldehyde (3.5 g, 21.1 mmol), 5-amino-2-methylpyridine (2.21 g, 20.5 mmol) dissolved in 70 ml toluene and 5 mg of TsOH contained in a flask connected to a Dean Stark apparatus was refluxed for 6 h. The solution was evaporated to dryness to give 5.4 g (100%) of an oil which was used directly for the next step. This compound (5.4 g, 21 mmol) dissolved in 20 ml DMF was added to a solution of t-butyldimethylsilyl chloride (4.76 g, 32 mmol) in 50 ml DMF, followed by imidazole (2.9 g, 42 mmol) and the resulting mixture was stirred at room temperature for 16 h. The mixture was poured into ice-water, neutralized by a 25% aqueous solution of ammonia and finally extracted with CH$_2$Cl$_2$. Evaporation of the dried solvent gave the crude Tbs protected imine as a brown oil (7.8 g, 100%). To 80 ml of dry THF placed in a two-necked flask were added n-butyllithium (26 ml of a 1.6 M solution in hexane, 42 mmol) and the resulting solution was stirred at −78° C. for 15 min. After the addition of diethyl methylphosphonate (6.4 g, 42 mmol) the mixture was stirred for 15 min at −78° C. then a THF solution of the Tbs protected imine (7.8 g, 21 mmol) was added dropwise and the resulting mixture was stirred at −78° C. for 90 min. The quenched reaction mixture (NH$_4$Cl solution) was extracted with diethyl ether, the dried ether extract (MgSO$_4$) was filtered and evaporated to give 11 g (100%) of the crude material as a brown oil. Glacial acetic acid (15 g, 253 mmol) was added to 60 ml of a TBF solution containing a mixture of diethyl β-(3-t-butyldimethylsilyloxy-5-methoxy-4-methylphenyl)-β-[N-(5-(2-methylpyridyl))-amino]-ethylphosphonate (11 g, 21 mmol) and tetrabutylammonium fluoride trihydrate (TBAF) (26.6 g, 84 mmol). After stirring at 20° C. for 3 h the reaction mixture was extracted with dichloromethane, the organic phase was washed (NaHCO$_3$), dried (MgSO$_4$) and evaporated. Purification by column chromatography (silica gel, 9/1 CH$_2$Cl$_2$/MeOH) gave after recrystallization from a mixture of petroleum ether/CH$_2$Cl$_2$ the title compound (1.6 g, 19%) as a light yellow solid, mp=138–140° C.

MS (m/e)=408: M$^+$, 301: M$^+$—C$_6$H$_6$N—NH, 257: M$^+$—CH$_2$—PO$_3$Et$_2$ (100%)

NMR (CDCl$_3$): δ=ca 9.5 (broad peak, 1H): O$\underline{H}$ 7.8, 6.80 (2d, 2H) and 6.64 (d, 1H): aromatic H, 5-pyridyl 6.56 and 6.38 (2m, 2H total): aromatic H, substituted phenyl 5.11(d, 1H):N—H 4.54–4.46 (m, 1H): C$\underline{H}$—CH$_2$—PO$_3$Et$_2$ 4.10–3.95 (m, 4H): P—O—C$\underline{H}_2$—CH$_3$ 3.82 (s, 3H): Ph-OC$\underline{H}_3$ 2.35 (s, 3H): Py-C$\underline{H}_3$ 2.31–2.18 (m, 2H): CH—C$\underline{H}_2$—PO$_3$Et$_2$ 2.08 (s,3H): Ph-C$\underline{H}_3$ 1.26 and 1.24 (2t, J=7 Hz, 6H total): P—O—CH$_2$—C$\underline{H}_3$ Example 14

Diethyl β-(3,5-dimethoxy-4-hydroxymethylphenyl)-β-[N-(5-(2-methylpyridyl))-amino]-ethylphosphonate

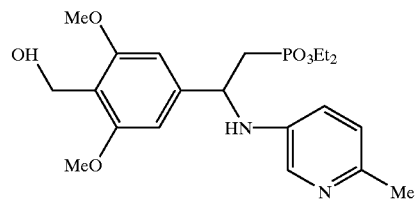

A mixture of 3.5 g (17.9 mmol) of 3,5-dimethoxy-4-hydroxymethylbenzaldehyde (mp=118–120°), 1.87 g (17.3 mmol) of 5-amino-2-methylpyridine and a catalytic amount of p-toluenesulfonic acid (ca. 10 mg) dissolved in 70 ml toluene contained in a flask connected to a Dean Stark apparatus was refluxed for 4 h. The toluene solution was evaporated to dryness to give 5.1 g (100%) of the crude imine. To a DMF solution (50 ml) of this material and t-butyldimethylsilyl chloride (4.03 g, 26.75 mmol) was added imidazole (2.43 g, 35.7 mmol) and the resulting mixture was stirred at room temperature for 16 h. The mixture was poured into ice water, neutralized by a 25% aqueous solution of ammonia and finally extracted with CH$_2$Cl$_2$. The organic phase was dried (MgSO$_4$), filtered and evaporated under vacuum to remove the last traces of DMF until constant weight. The Tbs protected imine was obtained as a brown oil (7.1 g, 99%) and was directly used in the next step. To 150 ml of dry TMF placed in a 500 ml two-necked flask were added n-butyllithium (22.3 ml of a 1.6 M solution in hexane, 35.7 mmol) and the resulting solution was stirred at −78° C. for 15 min. After the addition of diethyl methylphosphonate (5.4 g, 35.7 mmol) the mixture was stirred for 15 min at −78° C. then a THF solution of N-(5-(2-methylpyridyl)) 4-(t-butyldimethylsilyloxymethyl) 3,5-dimethoxybenzaldimine (7.1 g, 17.9 mmol) was added dropwise and the resulting mixture was stirred at −78° C. for 90 min. After a GLC check of a reaction sample has showed that the imine has reacted completely, hydrolysis was carried out with a saturated ammonium chloride solution. The quenched reaction mixture was extracted with diethyl ether, the dried ether extract ($MgSO_4$) was filtered and evaporated to dryness to 9.8 g (101%) of a light-brown oil.

Glacial acetic acid (13 ml) was added to 50 ml of a THF solution containing a mixture of diethyl β-(4-t-butyldimethylsilyloxy-3-methoxy-5-methylphenyl)-β-[N-5-(2-methylpyridyl))-amino]-ethylphosphonate (9.8 g, 18 mmol) and tetrabutylammonium fluoride trihydrate (TBAF) (22.4 g, 71 mmol). After stirring at 20° C. for 16 h a GLC test showed that the Tbs protected compound has not completely reacted. The reaction mixture was extracted with dichloromethane, the organic phase was washed with a saturated bicarbonate solution, dried over $MgSO_4$ and evaporated. The residue was then stirred for 4 h in a mixture of 2 ml trifluoroacetic acid and 70 ml of a 1% solution of HCl in ethanol. The reaction mixture was partitioned between a sodium bicarbonate solution and dichloromethane, the organic phase was separated and dried over $MgSO_4$. Purification by column chromatography (silica gel, 9/1 $CH_2Cl_2$/MeOH) gave 1.6 g (21%) of the title compound as an oil which slowly solidified.

MS (m/e)=438: $M^+$, 287: $M^+$—$CH_2PO_3Et_2$ NMR ($CDCl_3$): δ=7.90, 6.84 (2d, 1H each) and 6.68 (dd, 1H): aromatic H, 5-pyridyl 6.6 (s, 2H): aromatic H, substituted phenyl 5.18 (d, 1H, J=3 Hz): N—H 4.72 (s, 2H): HO—C$\underline{H}_2$-Ph 4.57–4.52 (m, 1H): C$\underline{H}$—$CH_2$—$PO_3Et_2$ 4.15–4.05 (m, 4H): P—O—C$\underline{H}_2$—$CH_3$ 3.81 (s, 6H): Ph-OC$\underline{H}_3$ 2.24 (dxd, J=7 and 15 Hz, 2H): CH—C$\underline{H}_2$—$PO_3Et_2$ 1.31 and 1.30 (2t, J=7 Hz): P—O—$CH_2$—C$\underline{H}_3$ Example 15

Summary of Synthesized Compounds

Table 1 summarizes aminophosphonates of formula (I), wherein $X^5$=H, m=0, n=0 and $Z^0$=H, herein designated formula (Ia), were prepared according to the processes hereinbefore described:

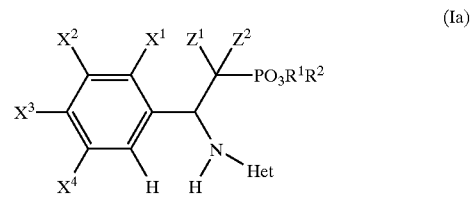

(Ia)

TABLE 1

| Cpd | $X^1$ | $X^2$ | $X^3$ | $X^4$ | $Z^1$ | $Z^2$ | Het | $R^1, R^2$ | mp (° C.) |
|---|---|---|---|---|---|---|---|---|---|
| 1 | H | OMe | OH | OMe | H | H | 3-pyridyl | Et | 164–166 |
| 2 | H | OMe | OH | OMe | H | H | 3-pyridyl | iPr | 138–140 |
| 3 | H | OMe | OH | OMe | H | H | 5-(2-methylpyridyl) | Et | 115–117 |
| 4 | H | OMe | OH | OMe | H | H | 5-(2-methylpyridyl) | iPr | 132–135 |
| 5 | H | OMe | OH | OMe | H | H | 3-(2,6-dimethylpyridyl) | Et | 152–154 |
| 6 | H | OMe | OH | OMe | H | H | 3-(2,6-dimethylpyridyl) | iPr | 118–120 |
| 7 | H | OMe | OH | OMe | H | H | 5-(2-methoxypyridyl) | Et | 128–130 |
| 8 | H | OMe | OH | OMe | H | H | 5-(2-methoxypyridyl) | iPr | 121–123 |
| 9 | H | OMe | OH | Me | H | H | 3-pyridyl | Et | 156–158 |
| 10 | H | OMe | OH | Me | H | H | 3-pyridyl | iPr | 135–137 |
| 11 | H | OMe | OH | Me | H | H | 5-(2-methylpyridyl) | Et | 173–175 |
| 12 | H | OMe | OH | Me | H | H | 5-(2-methylpyridyl) | iPr | 132–135 |
| 13 | H | OMe | OH | Me | H | H | 3-(2,6-dimethylpyridyl) | Me | Solid |
| 14 | H | OMe | OH | Me | H | H | 3-(2,6-dimethylpyridyl) | Et | 89–91 |
| 15 | H | OMe | OH | Me | H | H | 3-(2,6-dimethylpyridyl) | iPr | 81–83 |
| 16 | H | Me | OH | Me | H | H | 3-pyridyl | Et | 98–101 |
| 17 | H | Me | OH | Me | H | H | 3-pyridyl | iPr | 104–105 |
| 18 | H | OMe | OMe | OMe | H | H | 3-pyridyl | Et | 104–106 |
| 19 | H | OMe | OMe | OMe | H | H | 3-pyridyl | iPr | 96–98 |
| 20 | H | OEt | OH | Me | H | H | 3-pyridyl | Et | 162–164 |
| 21 | H | OEt | OH | Me | H | H | 3-pyridyl | iPr | 148–150 |
| 22 | H | OEt | OH | Me | H | H | 3-(2,6-dimethylpyridyl) | Et | 132–134 |
| 23 | H | OEt | OH | Me | H | H | 3-(2,6-dimethylpyridyl) | iPr | 95–96 |
| 24 | H | OH | OMe | OMe | H | H | 3-(2,6-dimethylpyridyl) | Et | 121–123 |
| 25 | H | OH | OMe | OMe | H | H | 3-(2,6-dimethylpyridyl) | iPr | 141–143 |
| 26 | H | OH | OMe | Me | H | H | 3-(2,6-dimethylpyridyl) | Et | 128–130 |
| 27 | H | OH | OMe | Me | H | H | 3-(2,6-dimethylpyridyl) | iPr | 168–170 |
| 28 | H | OMe | OH | Me | H | Me | 3-(2,6-dimethylpyridyl) | Et | 194–196 |

TABLE 1-continued

| Cpd | $X^1$ | $X^2$ | $X^3$ | $X^4$ | $Z^1$ | $Z^2$ | Het | $R^1, R^2$ | mp (° C.) |
|---|---|---|---|---|---|---|---|---|---|
| 29 | H | OMe | OH | Me | F | F | 3-(2,6-dimethylpyridyl) | Et | wax |
| 30 | H | t-Bu | OMe | t-Bu | H | H | 3-pyridyl | Et | wax |
| 31 | Me | OH | Me | H | H | H | 3-pyridyl | Et | solid |
| 32 | Me | OH | Me | H | H | H | 5-(2-methylpyridyl) | Et | solid |
| 33 | Me | OH | Me | H | H | H | 3-(2,6-dimethylpyridyl) | Et | solid |
| 34 | H | OH | Me | OMe | H | H | 3-pyridyl | Et | 146–147 |
| 35 | H | OH | Me | OMe | H | H | 5-(2-methylpyridyl) | Et | 138–140 |
| 36 | H | OH | Me | OMe | H | H | 3-(2,6-dimethylpyridyl) | Et | 168–170 |
| 37 | H | OMe | HO—CH$_2$ | OMe | H | H | 3-pyridyl | Et | solid |
| 38 | H | OMe | HO—CH$_2$ | OMe | H | H | 5-(2-methylpyridyl) | Et | solid |
| 39 | H | OMe | HO—CH$_2$ | OMe | H | H | 3-(2,6-dimethylpyridyl) | Et | solid |

Example 16

Biological Data

A. Lipoprotein(a) Lowering Activity

1. In vitro Data

The compounds of formula (I) were assayed for lowering the production of apo(a) in primary cultures of Cynomolgus hepatocytes.

Protocol: Hepatocytes were isolated from livers of male adult Cynomolgus monkeys by the two-step collagenase perfusion method according to C. Guguen-Guillouzo and A. Guillouzo "Methods for preparation of adult and fetal hepatocytes" p.1–12 in "Isolated and Cultured Hepatocytes," les editions Inserm Paris and John Libbey Eurotext London (1986).

The viability of cells was determined by Trypan blue staining. The cells were then seeded at a density of $1.5–2.10^5$ viable cells per 2 cm$^2$ in 24 well tissue culture plates in a volume of 500 µl per well of Williams E tissue culture medium containing 10% fetal calf serum. Cells were incubated for 6–24 hours at 37° C. in a CO$_2$ incubator (5% CO$_2$) in the presence of 20 µM of the test compounds dissolved in ethanol. Four wells were used for each compound. Nicotinic acid and steroid hormones were used as references to validate the assay system since they are known to decrease Lp(a) in man. Control cells were incubated in the presence of ethanol only.

The amount of Lp(a) secreted in culture medium was directly assayed by ELISA using a commercially available kit. Cells were washed and lysed as described by A. L. White et al., Journal of Lipid Research vol. 34, p. 509–517, (1993) and the cellular content of Lp(a) was assayed as described above. Changes in Lp(a) concentration in culture medium are given as the percentage of value measured for the control plates.

Results: The compounds No. 1, 2, 3, 4, 5, 6, 7, 8, 9, 10, 11, 12, 14, 15, 16, 17, 18, 19, 20, 21, 22, 23, 24, 25, 26, 27, 28, 29, 30, 31, 32, 33, 34, 35, 36, 37, 38 and 39 tested at 20 µM were found to lower the apo(a) secretion in the range between −10% to −35%.

2. In vivo Data

Study Protocol: Male cynomolgus monkeys weighing between 3 and 7 kg were divided into groups of 3 to 4 animals each. Prior to treatment their plasma Lp(a) levels were followed over a two-month period to ascertain a constant baseline value. Test compounds were given orally by gavage at the dose of 25 mg/kg/day for 4 weeks and Lp(a) was measured at day 28. At the end of the dosing period, animals were maintained for a treatment free period of 4 to 6 weeks, whereupon their plasma Lp(a) levels returned to pretreatment levels. This control provided proof that the decrease in Lp(a) measured was caused by the pharmacological activity of the test compounds. At Days −7 and 21 or 28, after an overnight fast blood samples were collected on EDTA and Lp(a) was measured by the highly sensitive and specific ELISA test. Results (mean of 3–4 values of each group ) were expressed as % of predose (Day −7).

Results: Selected compounds of formula (I) were tested under the experimental conditions to investigate their pharmacological activity in vivo. The compounds No 14 and 9 lower plasma Lp(a) in the range of −22% to −52% (values measured at Day 21 or 28,% changes from predose at Day −7).

B. Cholesterol Lowering Activity

Study Protocol: Male cynomolgus monkeys weighing between 3 and 7 kg were divided into groups of 3 to 4 animals each. Prior to treatment, their plasma cholesterol, LDL cholesterol and apo B levels were followed over a one-month period to ascertain a constant baseline value. Test compounds were given orally by gavage at the dose of 25 mg/kg/day for 4 weeks and apo B, LDL cholesterol, and total plasma cholesterol were measured at days 7, 14, 21 and 28. At the end of the dosing period, animals were maintained for a treatment-free period of 4 weeks, whereupon their cholesterol levels returned to pre-treatment levels. This control provided proof that the decrease in cholesterol measured was caused by the pharmacological activity of the test compounds. At Days −1 and 7, 14, 21 or 28, after an overnight fast, blood samples were collected on EDTA and apo B was measured by an ELISA method (Morwell diagnostics), LDL cholesterol by an immuno turbidimetric method (Boehringer) and total plasma cholesterol by an enzymatic method (CHOD-PAP, Boehringer). Results (mean of 3–4 values of each group) were expressed as % of pre-dose (Day −1).

Results: Selected compounds of formula (I) were tested under the experimental conditions described to investigate their pharmacological activity in vivo. The compounds No 14 and 9 lower apo B in the range from −16% to −45%, LDL cholesterol in the range from −10% to −22% and total plasma cholesterol from −10% to −25% (values measured at Day 21 or 28,% changes from pre-dose at Day −1).

What is claimed is:

1. A compound of formula (I):

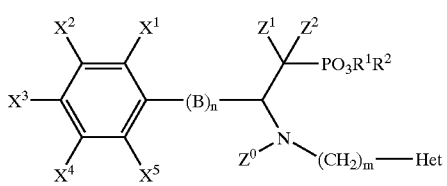

wherein $X^1$, $X^2$, $X^3$, $X^4$ and $X^5$ are independently hydrogen, hydroxy, hydroxymethyl, $C_1$–$C_2$ alkoxymethyl, a straight or branched $C_1$–$C_8$ alkyl group, a straight or branched $C_1$–$C_8$ alkoxy group; or $X^2$ may be combined with $X^3$ or $X^4$ may be combined with $X^5$ to form a 5- to 6-membered alkylidenedioxy ring optionally substituted with $C_1$–$C_4$ alkyl groups; or $X^4$ may be combined with $X^5$ to form a 5- to 6-membered alkylidene ring optionally substituted with $C_1$–$C_4$ alkyl groups;

$R^1$ and $R^2$ are independently hydrogen or a straight or branched $C_1$–$C_6$ alkyl group;

B is $CH_2$, $CH_2$—$CH_2$ or $CH$=$CH$;

n is zero or 1;

$Z^0$ is H, a straight or branched $C_1$–$C_4$ alkyl group, an acyl group $R^3$—CO where $R^3$ is an alkyl group from 1 to 4 carbon atoms, a $C_1$–$C_4$ perfluoroalkyl group;

$Z^1$, $Z^2$ are independently hydrogen, chloro, bromo, fluoro, a straight or branched $C_1$–$C_4$ alkyl group;

m is zero to 4;

Het is an optionally substituted heteroaryl group comprising at least one nitrogen atom;

or a pharmaceutically acceptable salt thereof.

2. The compound of claim 1, wherein $X^1$ is hydrogen or methyl; $X^2$ is methoxy, ethoxy, methyl or hydroxy; $X^3$ is hydrogen, hydroxy, methoxy, hydroxymethyl, methoxymethyl, methyl or ethyl; $X^4$ is hydrogen, methoxy or methyl and $X^5$ is hydrogen.

3. The compound of claim 2, wherein n is 0 or wherein n is 1 and B is $CH_2$.

4. The compound of claim 3, wherein $R^1$ and $R^2$ are independently $C_1$–$C_3$ alkyl.

5. The compound of claim 4, wherein $R^1$ and $R^2$ are independently ethyl or isopropyl.

6. The compound of claims 2, wherein m is zero.

7. The compound of claim 2, wherein $Z^1$ and $Z^2$ are hydrogen.

8. The compound of claim 2, wherein $Z^0$ is hydrogen.

9. The compound of any of claim 2, wherein Het is an optionally substituted pyridyl, pyrimidyl or pyrazyl.

10. The compound of claim 9, wherein Het is 3-pyridyl or 3-(2,6-dimethylpyridyl).

11. The compound of claim 1, wherein said compound of formula (I) is selected from the group consisting of:

diethyl β-(3,5-dimethoxy-4-hydroxyphenyl)-β-[N-(3-pyridyl)-amino]-ethylphosphonate;

diisopropyl β-(3,5-dimethoxy-4-hydroxyphenyl)-β-[N-(3-pyridyl)-amino]-ethylphosphonate;

diethyl β-(3,5-dimethoxy-4-hydroxyphenyl)-β-[N-5-(2-methoxypyridyl)-amino]-ethylphosphonate;

diisopropyl β-(3,5-dimethoxy-4-hydroxyphenyl)-β-[N-5-(2-methylpyridyl)-amino]-ethylphosphonate;

diethyl β-(3,5-dimethoxy-4-hydroxyphenyl)-β-[N-(3-(2,6-dimethyl)pyridyl))-amino]-ethylphosphonate;

diisopropyl β-(3,5-dimethoxy-4-hydroxyphenyl)-β-[N-(3-(2,6-dimethyl)pyridyl))-amino]-ethylphosphonate;

diethyl β-(3,5-dimethoxy-4-hydroxyphenyl)-β-[N-5-(2-methoxypyridyl)-amino]-ethylphosphonate;

diisopropyl β-(3,5-dimethoxy-4-hydroxyphenyl)-β-[N-5-(2-methoxypyridyl)-amino]-ethylphosphonate;

diethyl β-(4-hydroxy-3-methoxy-5-methylphenyl)-β-[N-(3-pyridyl)-amino]-ethylphosphonate;

diisopropyl β-(4-hydroxy-3-methoxy-5-methylphenyl)-β-[N-(3-pyridyl)-amino]-ethylphosphonate;

diethyl β-(4-hydroxy-3-methoxy-5-methylphenyl)-β-[N-5-(2-methylpyridyl)-amino]-ethylphosphonate;

diisopropyl β-(4-hydroxy-3-methoxy-5-methylphenyl)-β-[N-5-(2-methylpyridyl)-amino]-ethylphosphonate;

dimethyl β-(4-hydroxy-3-methoxy-5-methylphenyl)-β-[N-(3-(2,6-dimethyl)pyridyl)-amino]-ethylphosphonate;

diethyl β-(4-hydroxy-3-methoxy-5-methylphenyl)-β-[N-(3-(2,6-dimethyl)pyridyl)-amino]-ethylphosphonate;

diisopropyl β-(4-hydroxy-3-methoxy-5-methylphenyl)-β-[N-(3-(2,6-dimethyl)pyridyl)-amino]-ethylphosphonate;

diethyl β-(3,5-dimethyl-4-hydroxyphenyl)-β-[N-(3-pyridyl)-amino]-ethylphosphonate;

diisopropyl β-(3,5-dimethyl-4-hydroxyphenyl)-β-[N-(3-pyridyl)-amino]-ethylphosphonate;

diethyl β-(3,4,5-trimethoxyphenyl)-β-[N-(3-pyridyl)-amino]-ethylphosphonate;

diisopropyl β-(3,4,5-trimethoxyphenyl)-β-[N-(3-pyridyl)-amino]-ethylphosphonate;

diethyl β-(3-ethoxy-4-hydroxy-5-methylphenyl)-β-[N-(3-pyridyl)-amino]-ethylphosphonate;

diisopropyl β-(3-ethoxy-4-hydroxy-5-methylphenyl)-β-[N-(3-pyridyl)-amino]-ethylphosphonate;

diethyl β-(3-ethoxy-4-hydroxy-5-methylphenyl)-β-[N-(3-(2,6-dimethyl)pyridyl)]-ethylphosphonate;

diisopropyl β-(3-ethoxy-4-hydroxy-5-methylphenyl)-β-[N-(3-(2,6-dimethyl)pyridyl)]-ethylphosphonate;

diethyl β-(4,5-dimethoxy-3-hydroxyphenyl)-β-[N-(3-(2,6-dimethylpyridyl))-amino]-ethylphosphonate;

diisopropyl β-(4,5-dimethoxy-3-hydroxyphenyl)-β-[N-(3-(2,6-dimethylpyridyl))-amino]-ethylphosphonate;

diethyl β-(3-hydroxy-4-methoxy-5-methylphenyl)-β-[N-(3-(2,6-dimethylpyridyl))-amino]-ethylphosphonate;

diisopropyl β-(3-hydroxy-4-methoxy-5-methylphenyl)-β-[N-(3-(2,6-dimethylpyridyl))-amino]-ethylphosphonate;

diethyl β-(4-hydroxy-3-methoxy-5-methylphenyl)-β-[N-(3-(2,6-dimethyl)pyridyl))-amino]-α-methyl-ethylphosphonate;

diethyl β-(4-hydroxy-3-methoxy-5-methylphenyl)-β-[N-(3-(2,6-dimethyl)pyridyl))-amino]-α,α-difluoro-ethylphosphonate;

diethyl β-(3,5-di-tert-butyl-4-methoxyphenyl)-β-[N-(3-pyridyl)-amino]-ethylphosphonate;

diethyl β-(2,4-dimethyl-3-hydroxyphenyl)-β-[N-(3-pyridyl)-amino]-ethylphosphonate;

diethyl β-(2,4-dimethyl-3-hydroxyphenyl)-β-[N-(5-(2-methylpyridyl))-amino]-ethylphosphonate;

diethyl β-(2,4-dimethyl-3-hydroxyphenyl)-β-[N-(3-(2,6-dimethylpyridyl))-amino]-ethylphosphonate;

diethyl β-(3-hydroxy-5-methoxy-4-methylphenyl)-β-[N-(3-pyridyl)-amino]-ethylphosphonate;

diethyl β-(3-hydroxy-5-methoxy-4-methylphenyl)-β-[N-(5-(2-methylpyridyl))-amino]-ethylphosphonate;

diethyl β-(3-hydroxy-5-methoxy-4-methylphenyl)-β-[N-(3-(2,6-dimethylpyridyl))-amino]-ethylphosphonate;

diethyl β-(3,5-dimethoxy-4-hydroxymethylphenyl)-β-[N-(3-pyridyl)-amino]-ethylphosphonate;

diethyl β-(3,5-dimethoxy-4-hydroxymethylphenyl)-β-[N-(5-(2-methylpyridyl))-amino]-ethylphosphonate; and diethyl β-(3,5-dimethoxy-4-hydroxymethylphenyl)-β-[N-(3-(2,6-dimethylpyridyl))-amino]-ethylphosphonate.

12. A pharmaceutical composition comprising a therapeutically effective amount compound of claim 1 and a pharmaceutically acceptable excipient.

13. A method for decreasing plasma levels of apo (a), lipoprotein(a), apo B, LDL cholesterol and total cholesterol, comprising administration to a patient in need of such treatment of an effective amount of a compound of formula (I):

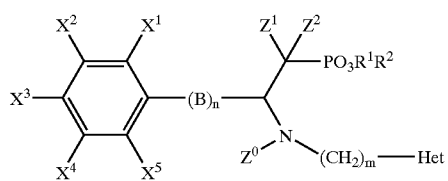

wherein $X^1$, $X^2$, $X^3$, $X^4$ and $X^5$ are independently hydrogen, hydroxy, hydroxymethyl, $C_1$–$C_2$ alkoxymethyl, a straight or branched $C_1$–$C_8$ alkyl group, a straight or branched $C_1$–$C_8$ alkoxy group; or $X^2$ may be combined with $X^3$ or $X^4$ may be combined with $X^5$ to form a 5- to 6-membered alkylidenedioxy ring optionally substituted with $C_1$–$C_4$ alkyl groups; or $X^4$ may be combined with $X^5$ to form a 5- to 6-membered alkylidene ring optionally substituted with $C_1$–$C_4$ alkyl groups;

$R^1$ and $R^2$ are independently hydrogen or a straight or branched $C_1$–$C_6$ alkyl group;

B is $CH_2$, $CH_2$—$CH_2$ or $CH$=$CH$;

n is zero or 1;

$Z^0$ is H, a straight or branched $C_1$–$C_4$ alkyl group, an acyl group $R^3$—CO where $R^3$ is an alkyl group from 1 to 4 carbon atoms, a $C_1$–$C_4$ perfluoroalkyl group;

$Z^1$, $Z^2$ are independently hydrogen, chloro, bromo, fluoro, a straight or branched $C_1$–$C_4$ alkyl group;

m is zero to 4;

Het is an optionally substituted heteroaryl group comprising at least one nitrogen atom;

or a pharmaceutically acceptable salt thereof.

14. A method for the prevention of thrombus formation comprising administration to a patient in need of such treatment an anticoagulating effective amount of a compound of formula (I):

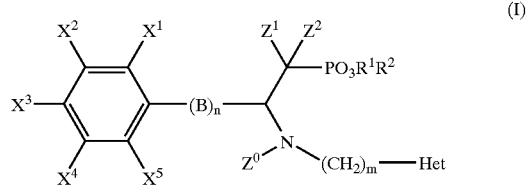

wherein $X^1$, $X^2$, $X^3$, $X^4$ and $X^5$ are independently hydrogen, hydroxy, hydroxymethyl, $C_1$–$C_2$ alkoxymethyl, a straight or branched $C_1$–$C_8$ alkyl group, a straight or branched $C_1$–$C_8$ alkoxy group; or $X^2$ may be combined with $X^3$ or $X^4$ may be combined with $X^5$ to form a 5- to 6-membered alkylidenedioxy ring optionally substituted with $C_1$–$C_4$ alkyl groups; or $X^4$ may be combined with $X^5$ to form a 5- to 6-membered alkylidene ring optionally substituted with $C_1$–$C_4$ alkyl groups;

$R^1$ and $R^2$ are independently hydrogen or a straight or branched $C_1$–$C_6$ alkyl group;

B is $CH_2$, $CH_2$—$CH_2$ or $CH$=$CH$;

n is zero or 1;

$Z^0$ is H, a straight or branched $C_1$–$C_4$ alkyl group, an acyl group $R^3$—CO where $R^3$ is an alkyl group from 1 to 4 carbon atoms, a $C_1$–$C_4$ perfluoroalkyl group;

$Z^1$, $Z^2$ are independently hydrogen, chloro, bromo, fluoro, a straight or branched $C_1$–$C_4$ alkyl group;

m is zero to 4;

Het is an optionally substituted heteroaryl group comprising at least one nitrogen atom;

or a pharmaceutically acceptable salt thereof.

15. A method for the prevention of restenosis following angioplasty, comprising administration of an amount effective to decrease plasma levels of apo (a) and lipoprotein(a) of a compound of formula (I):

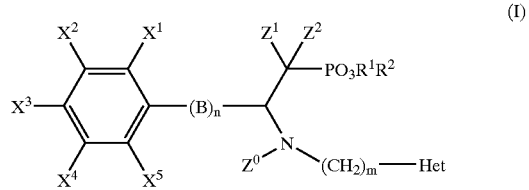

wherein $X^1$, $X^2$, $X^3$, $X^4$ and $X^5$ are independently hydrogen, hydroxy, hydroxymethyl, $C_1$–$C_2$ alkoxymethyl, a straight or branched $C_1$–$C_8$ alkyl group, a straight or branched $C_1$–$C_8$ alkoxy group; or $X^2$ may be combined with $X^3$ or $X^4$ may be combined with $X^5$ to form a 5- to 6-membered alkylidenedioxy ring optionally substituted with $C_1$–$C_4$ alkyl groups; or $X^4$ may be combined with $X^5$ to form a 5- to 6-membered alkylidene ring optionally substituted with $C_1$–$C_4$ alkyl groups;

$R^1$ and $R^2$ are independently hydrogen or a straight or branched $C_1$–$C_6$ alkyl group;

B is $CH_2$, $CH_2$—$CH_2$ or $CH$=$CH$;

n is zero or 1;

$Z^0$ is H, a straight or branched $C_1$–$C_4$ alkyl group, an acyl group $R^3$—CO where $R^3$ is an alkyl group from 1 to 4 carbon atoms, a $C_1$–$C_4$ perfluoroalkyl group;

$Z^1$, $Z^2$ are independently hydrogen, chloro, bromo, fluoro, a straight or branched $C_1$–$C_4$ alkyl group;

m is zero to 4;

Het is an optionally substituted heteroaryl group comprising at least one nitrogen atom;

or a pharmaceutically acceptable salt thereof.

16. A method for the prevention of development of atherosclerosis, comprising administration to a patient in need of such treatment an effective amount of a compound formula (I):

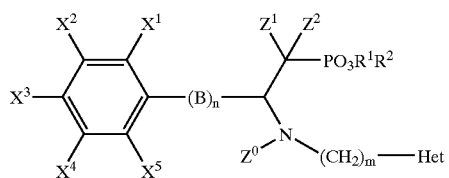

(I)

wherein $X^1$, $X^2$, $X^3$, $X^4$ and $X^5$ are independently hydrogen, hydroxy, hydroxymethyl, $C_1$–$C_2$ alkoxymethyl, a straight or branched $C_1$–$C_8$ alkyl group, a straight or branched $C_1$–$C_8$ alkoxy group; or $X^2$ may be combined with $X^3$ or $X^4$ may be combined with $X^5$ to form a 5- to 6-membered alkylidenedioxy ring optionally substituted with $C_1$–$C_4$ alkyl groups; or $X^4$ may be combined with $X^5$ to form a 5- to 6-membered alkylidene ring optionally substituted with $C_1$ to $C_4$ alkyl groups;

$R^1$ and $R^2$ are independently H, a straight or branched alkyl group having from 1 to 6 carbon atoms;

B is $CH_2$, $CH_2$—$CH_2$ or $CH$=$CH$;

n is zero or 1;

$Z^0$ is H, a straight or branched alkyl group having from 1 to 4 carbon atoms, an acyl group $R^3$—CO where $R^3$ is an alkyl group from 1 to 4 carbon atoms, a perfluoroalkyl group from 1 to 4 carbon atoms;

$Z^1$, $Z^2$ are independently H, Cl, Br, F, a straight or branched alkyl group from 1 to 4 carbon atoms;

m is zero to 4;

Het is an optionally substituted heteroaryl group comprising at least one nitrogen atom;

or a pharmaceutically acceptable salt thereof.

* * * * *